(12) United States Patent
Zhang et al.

(10) Patent No.: US 8,399,239 B2
(45) Date of Patent: Mar. 19, 2013

(54) COMPOSITIONS AND METHODS FOR CONTINUOUS HARVESTING OF SUSPENSION GROWTH CULTURES

(75) Inventors: Tianxi Zhang, Fort Collins, CO (US); Richard Crowell, Fort Collins, CO (US)

(73) Assignee: Solix Biofuels, Inc., Fort Collins, CO (US)

( * ) Notice: Subject to any disclaimer, the term of this patent is extended or adjusted under 35 U.S.C. 154(b) by 10 days.

(21) Appl. No.: 13/072,527

(22) Filed: Mar. 25, 2011

(65) Prior Publication Data

US 2011/0263002 A1    Oct. 27, 2011

Related U.S. Application Data

(60) Provisional application No. 61/317,863, filed on Mar. 26, 2010.

(51) Int. Cl.
*C12N 1/12* (2006.01)
(52) U.S. Cl. .................... 435/252.1; 435/257.1
(58) Field of Classification Search ............... 435/252.1, 435/257.1
See application file for complete search history.

(56) References Cited

U.S. PATENT DOCUMENTS 4,554,390 A      11/1985   Curtain et al.
2011/0081706 A1*  4/2011   Schlesinger et al. ....... 435/252.1

OTHER PUBLICATIONS

Yadidla, et al., "Algae Removal by High Gradient Magnetic Filtration," Env. Health Lab., Graduate School of applied Science and Technology, Hebrew University, vol. 11, No. 9, Sep. 1977.
Ayoub, et al., "Seawater Induced Algal Flocculation," Wat. Res. vol. 20, No. 10, pp. 1265-1271, 1986.
Ayoub, et al., "Algal Separation by the Lime-Seawater Process," Journal Water Pollution Control Federation, vol. 58, No. 9, Conference Issue, Sep. 1986.
Yahi, et al., "Algal Flocculation-Sedimentation by pH Increase in a Continuous Reactor," Water Science Tech., vol. 30, No. 8, pp. 259-267, 1994.
Semerjian, et al., "High-pH-Magnesium Coagulation—Flocculation in Wastewater Treatment," Elsevier Science Ltd., Advances in Environmental Research 7, pp. 389-403, 2003.
Mirnezami, et al., "Mechanism of Aggregation of Silica by Magnesium Ions: A Technical Note," Canadian Metallurgical Quarterly, vol. 43, No. 4 pp. 521-526, 2004.

\* cited by examiner

*Primary Examiner* — Karen Cochrane Carlson
*Assistant Examiner* — Natalie Moss
(74) *Attorney, Agent, or Firm* — Faegre Baker Daniels LLP

(57) ABSTRACT

Embodiments herein concern compositions, methods and uses for harvesting suspension cultures or decontaminating waters. In certain embodiments, suspension microorganism cultures can comprise algal cultures. In some embodiments, harvesting suspension cultures may include using a composition capable of interacting with the culture in order to separate the culture from a liquid or media.

9 Claims, 19 Drawing Sheets

A.

Fe$_3$O$_4$ = 2.0 % (w/v), pH = 10.3

B.

Fe$_3$O$_4$ = 5.0 % (w/v), pH = 10.3

C.

Fe$_3$O$_4$ = 7.6 % (w/v), pH = 10.3

D.

Fe$_3$O$_4$ = 10.3 % (w/v), pH = 10.3

A.      B.      C.

A.      B.

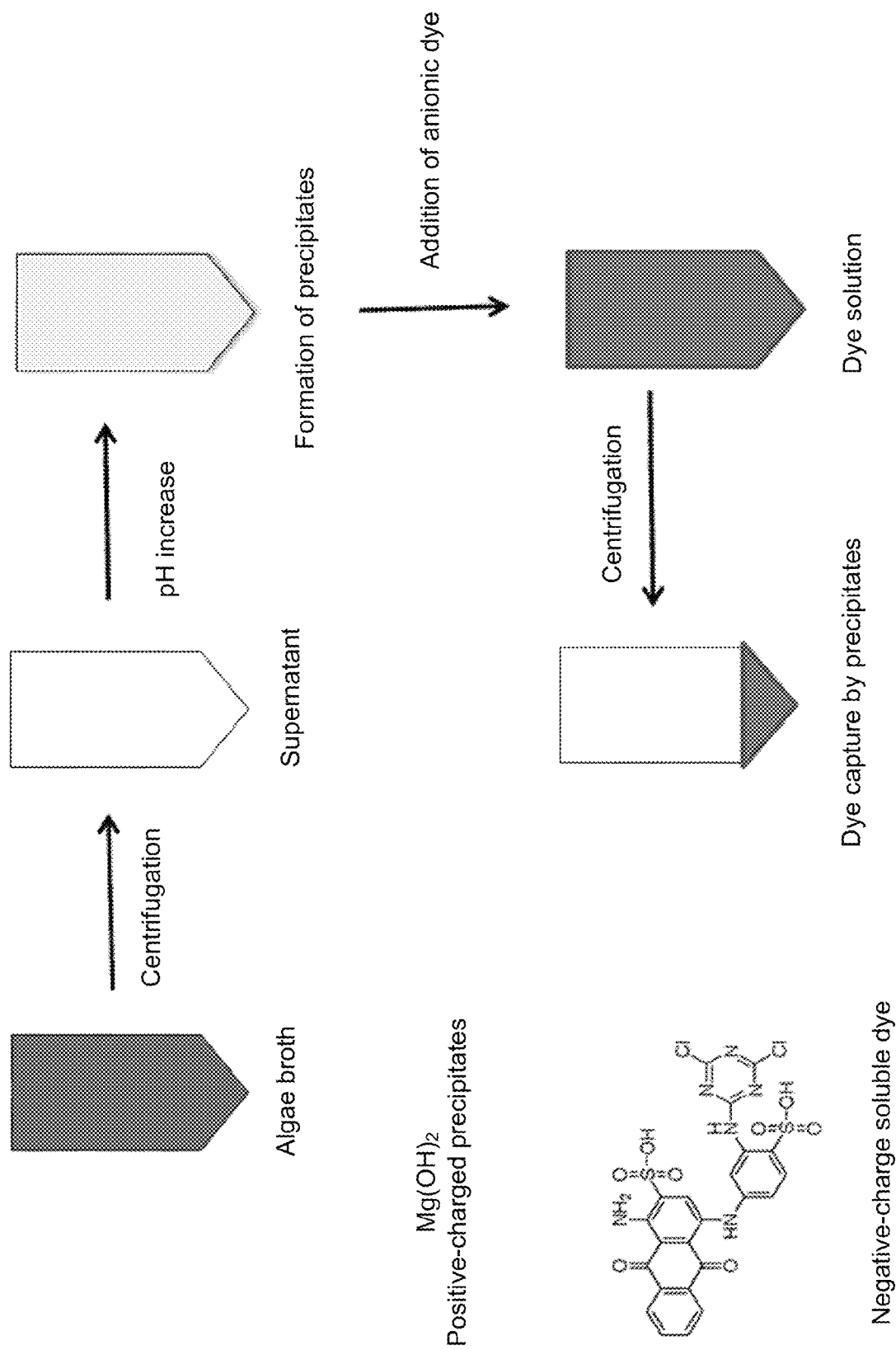

A.  B.

Fig. 12
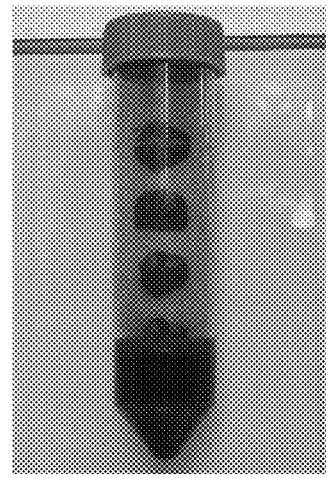
Recovered pH 6.6
Figs. 13A-13B
A.
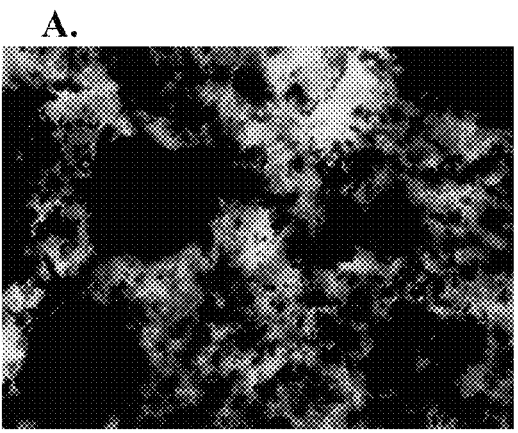
Before: pH 10.5 ($Fe_3O_4$=2.0 % (w/v))
B.
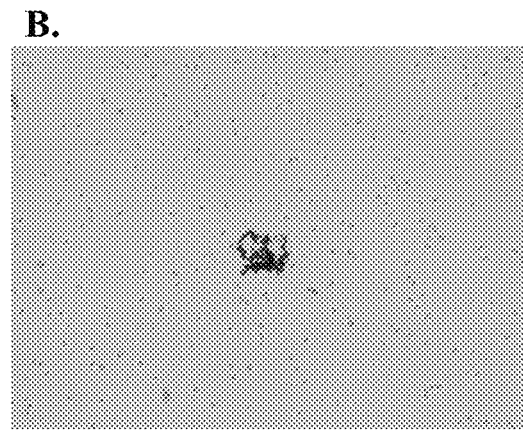
After: pH 6.6

Settled 1.5 min    Settled 3.5 min    Settled 10.5 min    Settled 23 min    Settled 31 min (10x)     (40x)

A. Raw *N. salina* (pH 10.6)

(10x)     (40x)

B. Separator Influent (10x)　　　(40x)

C. Effluent before Settling (10x)　　　(40x)

D. Effluent after Settling

Raw algae broth #1: 90.8 liters
Raw algae broth #2: 50.0 liters
Supernatant effluent: 113.17 liters
Recovered algae broth: 18.93 liters
Recovered algae broth: 16.28 liters
Recovered #3 (5x dilution) was obtained from recovered magnetite slurry

A.

B.

scale bar of 20 μm

COMPOSITIONS AND METHODS FOR CONTINUOUS HARVESTING OF SUSPENSION GROWTH CULTURES

CROSS REFERENCE TO RELATED APPLICATIONS

The present application claims the benefit under 35 U.S.C. 119(e) of U.S. Provisional Patent Application Ser. No. 61/317,863 filed on Mar. 26, 2010 which is incorporated herein by reference in its entirety for all purposes.

FIELD OF THE INVENTION

Embodiments of the present invention generally report methods and compositions for suspension cultures or waste waters. In certain embodiments, compositions and methods concern separating algae from a media or liquid. Other embodiments concern compositions, methods and uses of a harvesting system or harvesting agent for removing media compositions from suspension cultures and reusing the harvesting agent. Yet other embodiments may concern systems and methods for separating biomass from algae media for use in biofuels production and generation of related algal products.

BACKGROUND

Chemical Coagulation and Flocculation for Algae Harvesting

Algae harvesting can be challenging for algae biofuels production due in part to few cost-effective technologies available. One current technology is chemical coagulation and flocculation, widely applied in water and wastewater treatment. Coagulants typically function as neutralization of surface charges of suspended particles in water. Neutralized particles are typically still suspended in water as the coagulated particles do not aggregate together to form big flocs. Thus, polymer flocculants are added to bridge the neutralized particles for formation of big flocs to permit settling out of the coagulates. Some polymer flocculants are expensive even at low dose for algae harvesting.

SUMMARY

Embodiments of the present invention generally report methods and compositions for suspension cultures. In certain embodiments, compositions and methods concern separating suspension cultures (e.g. algae) from a media. Other embodiments concern compositions, methods and uses of a harvesting system for removing media compositions from suspension cultures. Yet other embodiments may concern systems and methods for separating biomass from algae media for use in biofuel production and generation of related algal products. Some embodiments concern suspension cultures or wastewaters including, but not limited to algae, bacteria, yeast, fungi, suspended solids in water and wastewater particulates.

Certain embodiments of the present invention report magnetic flocculation for harvesting a suspension culture or particulate/microorganism removal from waters (e.g. wastewater). In accordance with these embodiments, a culture may be an algal culture. For example, algae can be adsorbed on surfaces of magnetite particles, forming magnetically-linked algae complexes capable of removal from growth media. In certain embodiments, the magnetically-linked algae may be separated from a media using a magnetic separator or sedimentation, such as by gravity or magnetic field. In certain embodiments, algae and magnetite particles have a negative charge in some media, which can result in an electrostatic repulsion between them. Algae adsorption on magnetite particles should have an attractive interaction to occur. Either algae or magnetite can be changed into positively charged elements.

In certain embodiments, media for algae (e.g. for *Nannochloropsis oculata*, *Nannochloropsis salina* or other algae) cultivation can have high concentrations of magnesium ions (e.g. 600 mg/L, 1,000 mg/L or 2,000 mg/L or other) from inorganic salts for the algal growth. Precipitation of magnesium hydroxides can occur at high pH (e.g. about 8.5 to about 11.5, about 9.0 to about 11.0, about 9.5 to about 10.5) in media. Other solution pHs are contemplated for use in precipitation of magnesium hydroxides. In some embodiments, positively charged magnesium hydroxide precipitates in suspension media can bind with both negatively charged algae and magnetite based on electrostatic attraction to form particle-algae complexes. In accordance with these embodiments, particle-algae complexes can be captured by a magnetic field (e.g. a magnet), concentrating the algae and separating the algae from media or using other methods such as gravity. In certain embodiments, magnesium hydroxides can flocculate algae at a high pH (e.g. about 8.5 to about 11.5, about 9.0 to about 11.0, about 9.5 to about 10.5). Magnetite particles can tag algae to provide a magnetic property, resulting in algal movement/attraction under a magnetic field. In addition, particle-algae complexes can have a higher density than non-particle algae. For example, magnetite density can be about 5.0 g/cm$^3$ to about 5.5 g/cm$^3$. In certain embodiments, some heavier flocculated algae can settle out of solution by gravity. This process can produce less sludge in the flocculation process.

In certain embodiments, agents used for flocculation or coagulation can include, but are not limited to, iron oxides (e.g. magnetite ($Fe_3O_4$), maghemite ($Fe_2O_3$), $FeO \cdot Fe_2O_3$,)) iron, steel, silica (sand), tungsten, magnesium (e.g. magnesium chloride, magnesium hydroxides, seawater), base (e.g. sodium hydroxides, lime), acid (e.g. hydrochloric acid). In some embodiments, organic materials of use in certain methods described herein can include, but are not limited to, fiber, starch, wood, or polymers. In other embodiments, composite materials can include, but are not limited to, carbon-fiber, glass-plastics, silica-polymers, metal-polymers, ceramic-polymers, and clay-polymers. In yet other embodiments, agents of use to modify pH can include, but are not limited to, chemical agent, a gas (e.g. air for pH increase, $CO_2$ for pH decrease), or other suitable agent capable of modifying pH of a suspension culture in order to facilitate flocculation of the culture or other matter. Some embodiments can include agents capable of easy manipulation or that are easy to eliminate from the suspension as necessary.

In certain methods disclosed herein, magnetic flocculation can be a simple and efficient method to separate algae (e.g. *Nannochloropsis oculata* and *Nannochloropsis salina*) from media. In one embodiment a suspension culture can be tagged with a magnetic or heavy material. The tagging magnetic or heavy material can include, but are not limited to, iron oxide, tungsten, silicon, magnetic material aluminum hydroxide, iron, iron sulfate, sand or other suitable heavy material. In accordance with these embodiments, the tagging or heavy material can be added at a basic pH where precipitates can be formed. A basic pH contemplated for some embodiments herein can include a pH of about 8.5 to about 11.5, about 9.0 to about 11.0, about 9.5 to about 10.5.

In one embodiment, algae can be tagged with iron oxide particles at a basic pH to form magnesium hydroxide precipitates. In certain embodiments, pH of a media or solution can have an effect on harvesting performance. For example, algae can be harvested (e.g. about 97%) through the enhanced settling by a magnetic separator. In accordance with this example, about 90% of media could be removed by gravity sedimentation of the magnetic algae. In other embodiments, suspension cultures precipitated or drawn to a magnetic separator may be concentrated. Some examples concern concentrating algae associated with magnetic particles. In other embodiments, compositions and methods can be used to separate cultures from the magnetic or heavy particles using a gradual or sharp adjustment in pH. In certain embodiments, the pH may be decreased to pH of about 6.0 to a pH of about 7.5. In addition, materials of use to precipitate and/or concentrate suspension cultures may be recycled for reuse.

In other embodiments, magnetic flocculation for harvesting a microorganism contemplated herein can be performed without base addition and adjustment of the pH. In other embodiments, agents used for flocculation or coagulation, iron oxides (e.g. magnetite ($Fe_3O_4$), maghemite ($Fe_2O_3$), $FeOFe_2O_3$) iron, steel, silica (sand), tungsten, magnesium (e.g. magnesium chloride, magnesium hydroxides, seawater), base (e.g. sodium hydroxides, lime), acid (e.g. hydrochloric acid) can be added to a culture from about 500 mg/L to about 2500 mg/L and pH can be adjusted as necessary to induce flocculation. In one embodiment, magnesium can be added to a culture at about 2,000 mg/L and pH adjusted to about 9.5 wherein subsequent algae harvesting can be about 99% recovery of the algae.

In certain embodiments, compositions contemplated herein may concern suspension cultures or wastewaters in combination with magnetic or heavy particles at a basic pH for precipitation/concentration followed by a more neutral or slightly acidic pH allowing separation of the cultures.

In some embodiments, magnetic or heavy particles may be collected and regenerated for use in another suspension culture or waste water. In other embodiments, continuous culturing and concentrating techniques disclosed herein may be used for cost effective and rapid suspension culture harvesting.

BRIEF DESCRIPTION OF THE DRAWINGS

In the following sections, various exemplary compositions and methods are described in order to detail various embodiments. It will be obvious to one skilled in the art that practicing the various embodiments does not require the employment of all or even some of the details outlined herein, but rather that concentrations, times and other details may be modified through routine experimentation. In some cases, well-known methods or components have not been included in the description.

FIG. 5 represents a schematic of a procedure using a dye indicator during a flocculation process.

FIG. 12 illustrates recovered magnetite at a reduced pH.

FIGS. 13A-13B represents microscopic images of before and after the magnetite removal.

DEFINITIONS

Figure 1:
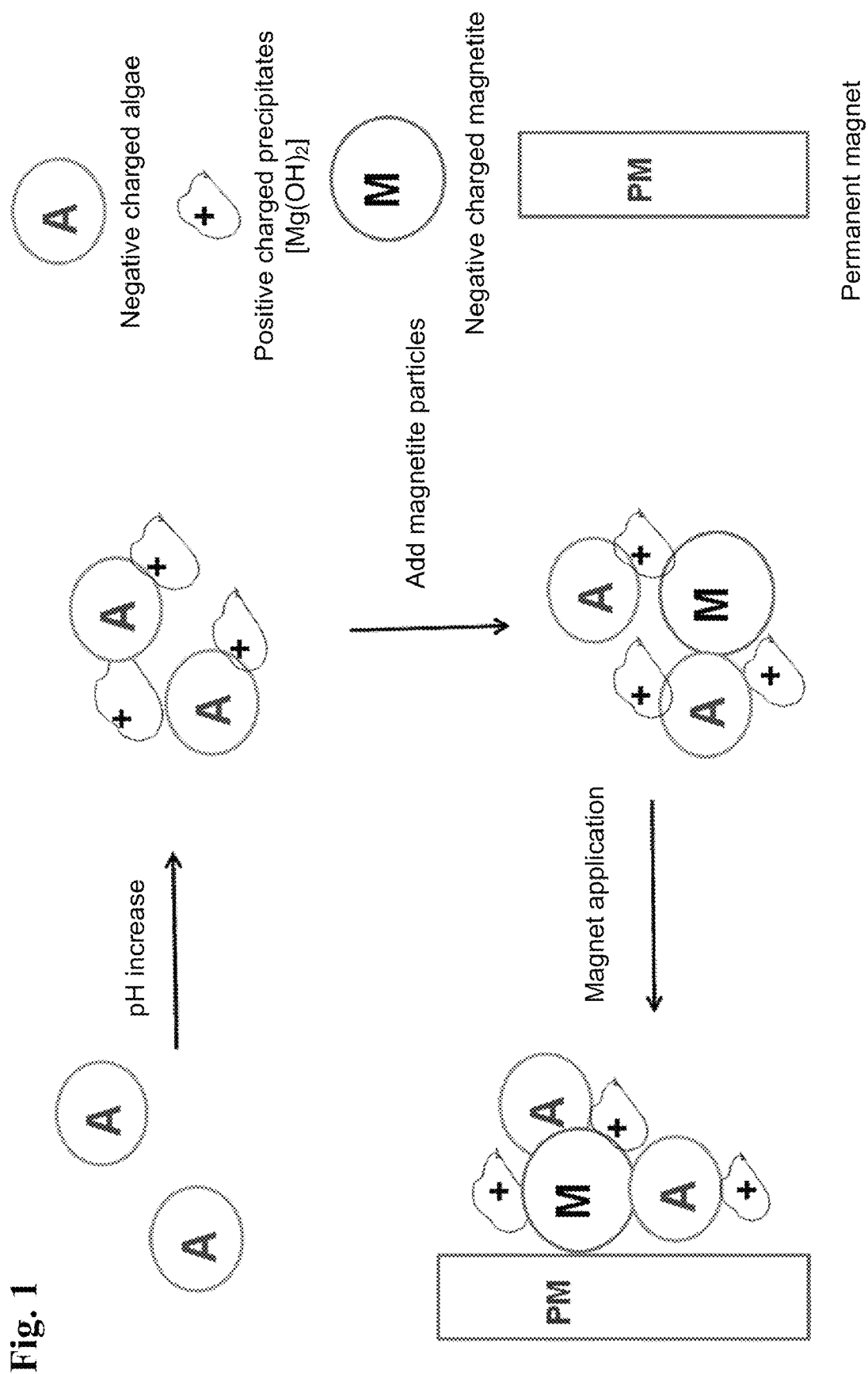
FIG. 1 represents a schematic diagram of the magnetic flocculation.
Figure 2A:
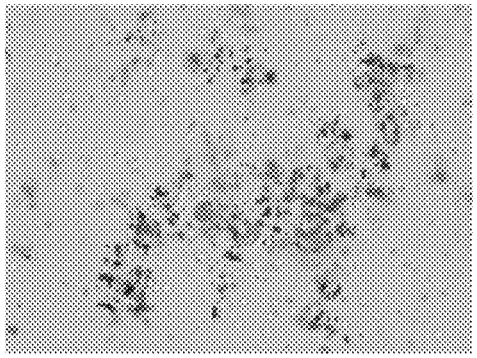
FIG. 2 represents microscopic images of magnetite dispersion in suspension cultures at basic pH.
Figure 2B:
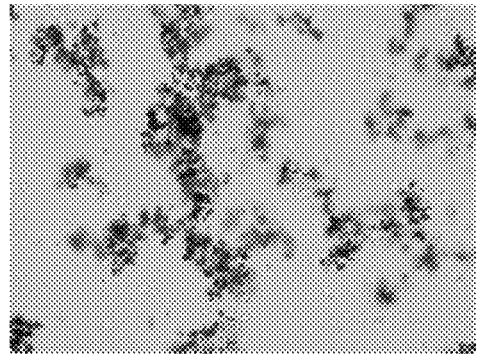
Figure 2C:
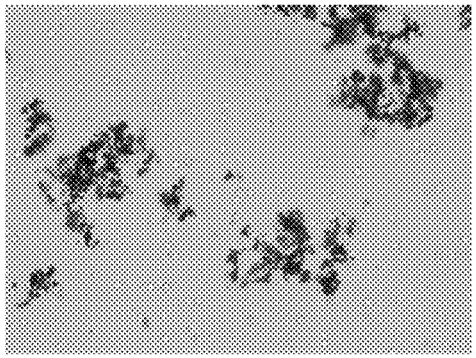
Figure 2D:
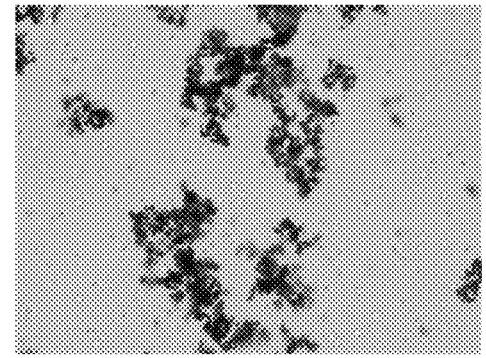

As used herein, "a" or "an" may mean one or more than one of an item.

As used herein, "about" may mean up to and including plus or minus five percent, for example, about 100 may mean 95 and up to 105.

As used herein, "tag," "tagging" or "tagged" may mean attaching a particle or agent to a microorganism. For example, a tagged alga can be algae attached to a particle for harvesting or other purpose as described herein.

DETAILED DESCRIPTION

In the following sections, various exemplary compositions and methods are described in order to detail various embodiments. It will be obvious to one skilled in the art that practicing the various embodiments does not require the employment of all or even some of the details outlined herein, but rather that concentrations, times and other specific details may be modified through routine experimentation. In some cases, well-known methods or components have not been included in the description.

Embodiments herein represent methods, and compositions for harvesting and using harvest suspension culture yields. In some embodiments, the cultures can be algae, bacteria, fungi or yeast cultures. Products contemplated herein for production from the algal yields can include, but are not limited to, biofuels, protein, vitamins, carbohydrates and/or amino acids.

In certain embodiments, particles or heavy materials may be used as coagulants or concentrators of suspension cultures or wastewaters (e.g. for removal of particulates or microorganisms). For example, in some embodiments, microorganisms can associate with particles or heavy materials by adjusting the condition of the culture media in order to harvest the microorganisms.

Previously, it was demonstrated that adsorbed algae particles can be removed from water by a magnetic field. Algae were removed by passing through a high gradient magnetic filtration (HGMF). In this study about 90% of algae were removed at 500-1,200 mg/L of magnetite as magnetic seeds in laboratory batch experiments. One of the problems of this method was that removal of the algae required a large concentration of iron ions as a primary coagulant and iron coagulants tended to modify the algae surfaces reducing production of the algae and the coagulants could not be recycled for reuse making it an expensive process.

In some embodiments, algae surfaces can be modified prior to adsorption using methods disclosed herein. In certain embodiments, algal suspension cultures can be changed to hydrophobic cultures prior to harvesting. In accordance with these embodiments, magnetite particles often do not meet such a hydrophobic requirement for association, so magnetite particles can be modified to be hydrophobic using, for example, a silanization reaction. Algal cells can be adsorbed on the magnetite surfaces and algae-magnetite complex particles can be removed from the solution using for example, a magnet. Thus, algae can be harvested from any solution, for example, a media or other liquid. However, this method requires the silanized hydrophobic magnetite, which leads to an expensive process. In addition, treated algae also should be hydrophobic surfaces, which might not be achieved for many species of algae.

Some embodiments of the present invention concern algae harvesting using flocculation or coagulation techniques. In certain embodiments, methods disclosed herein may concern magnesium hydroxide flocculation. In accordance with these embodiments, when magnesium ions are present in a solution, an increase in pH can lead to precipitation of magnesium hydroxides [Mg(OH)$_2$] shown in the equation (1) below, previously submitted.

$$Mg^{2+} + 2OH^- = Mg(OH)_2\downarrow \qquad (1)$$

Solution pH plays a key role in magnesium hydroxide precipitation. The figure below represents magnesium hydroxide precipitation as a function of pH. The precipitation starts at approximately pH 9.5 and completes at approximately pH 11.5. In certain embodiments, an elevated pH may be about 9.0 to about 12.0, or about pH 9.5 to about 11.5. Magnesium hydroxides are gelatinous precipitates that carry positive charges. The mechanism of magnesium hydroxide flocculation is at least in part an electrostatic bridging where positively charged magnesium hydroxide precipitates flocculate negative charged particles. Distribution diagram of magnesium ions and magnesium hydroxides can be shown as a function of pH. [diagram not shown]

In certain embodiments, algal flocculation methods and compositions were used in the presence of magnesium at basic pH levels as indicated above.

It has been demonstrated that algal flocculation occurs at high pH (e.g. about 9.0 to about 11.5). Algal flocculation can occur by adding seawater in concentration of about 5-10% (v/v). Both negatively charged calcium carbonate (CaCO$_3$) and positively charged Mg(OH)$_2$ could be precipitated at higher pH (e.g. 10.2) when lime was added. A continuous fluidized reactor was designed and tested. High suspended solid removal (e.g. 95%) was reportedly obtained at pH values of 11.8-12.0. One of the problems with these approaches was large amounts of sludge, however, were generated in use of magnesium hydroxide precipitates, which can hinder adoption of this process for commercialization application. Gelatinous precipitates of magnesium hydroxides might lead to increased formation of sludge in a loose structure. Therefore, eliminating or reducing the sludge problem was a follow-on issue.

Embodiments herein present solutions to alleviate or reduce generation of sludge or other issues faced by some of these previously disclosed methods. In some embodiments herein, algae can be separated by using magnetic separation technologies followed by, for example, changes in compositions in order to harvest the cultures. In some embodiments, solution pH may be adjusted in order to facilitate interaction between a culture (or contaminant) and magnetite (e.g. using a base, such as sodium hydroxide). Magnetite (Fe$_3$O$_4$) particles at different concentrations and particle sizes can be added to algae cultures. Subsequently, a permanent magnet can be applied to remove flocculated algae. Then, the magnetite can be recovered, by a solution pH decrease, by addition of for example, an acid (e.g. hydrochloric acid) where the magnesium hydroxide precipitates were dissolved in solution, following that an electrostatic repulsion between the algae and the magnetite occurred. Concentrated algae can be obtained by decanting supernatant when applying a magnetic field.

In some embodiments, a suspension culture can include, but is not limited to, algae, bacteria, yeast, and fungi. Other embodiments can include removal of suspended solids or microorganisms in water and wastewater clean-up or contaminant removal.

Algal strains contemplated for harvesting or concentration herein can include, but are not limited to, *Phaeodactulum tricornutum, Chlorella protothecoides, Nannochloropsis salina, Nannochloropsis* sp, *Tetraselmis succica, Tetraselmis chuii, Botrycoccus braunii, Chlorella* sp., *Chlorella ellipsoidea, Chlorella emersonii, Chlorella minutissima, Chlorella salina, Chlorella protothecoides, Chlorella pyrenoidosa, Chlorella sorokiniana, Chlorella vulgaris, Chroomonas salina, Cyclotella cryptica, Cyclotella* sp., *Dunaliella salina, Dunaliella bardawil, Dunaliella tertiolecta, Euglena gracilis, Gymnodinium nelsoni, Haematococcus pluvialis, Isochrysis galbana, Monoraphidium minutum, Monoraphidium* sp., *Neochloris oleoabundans, Nitzschia laevis, Onoraphidium* sp., *Pavlova lutheri, Phaeodactylum tricornutum, Porphyridium cruentum, Scenedesmus obliquuus, Scenedesmus quadricaula Scenedesmus* sp., *Stichococcus bacillaris, Spirulina platensis, Thalassiosira* sp. or combinations thereof. In other embodiments, methods and compositions disclosed herein may be used to harvest cyanobacteria or other suspension prokaryotic or eukaryotic cultures.

Agents capable of coagulating or of use as a flocculant include, but are not limited to, iron oxides (e.g. magnetite (Fe$_3$O$_4$), maghemite (Fe$_2$O$_3$)), iron, steel, silica (sand), tungsten, and magnesium agents (e.g. magnesium chloride, magnesium hydroxides, seawater).

Solutions of use to modulate pH of a composition can include base (e.g. sodium hydroxides, lime), acid (e.g. hydrochloric acid), gas (e.g. air for pH increase, CO$_2$ for pH decrease) or other suitable agent.

In certain embodiments, media for algae (e.g. for *Nannochloropsis oculata, Nannochloropsis salina* or other algae) cultivation can have high concentrations of magnesium ions (e.g. 600 mg/L, 1,000 mg/L or 2,000 mg/L or other) from inorganic salts for the algal growth. Precipitation of magnesium hydroxides can occur at high pH (e.g. about 8.5 to about 11.5, about 9.0 to about 11.0, about 9.5 to about 10.5) in media. Other solution pHs are contemplated for use in precipitation of magnesium hydroxides. In some embodiments, positively charged magnesium hydroxide precipitates in suspension media can bind with both negatively charged algae and magnetite based on electrostatic attraction to form particle-algae complexes. In accordance with these embodiments, particle-algae complexes can be captured by a magnetic field (e.g. a magnet), concentrating the algae and separating the algae from media or using other methods such as gravity. In certain embodiments, magnesium hydroxides can flocculate algae at a high pH (e.g. about 8.5 to about 11.5, about 9.0 to about 11.0, about 9.5 to about 10.5). Magnetite particles can tag algae to provide a magnetic property, resulting in algal movement/attraction under a magnetic field. In addition, particle-algae complexes can have a higher density than non-particle algae. For example, magnetite density can be about 5.0 g/cm$^3$ to about 5.5 g/cm$^3$. In certain embodiments, some heavier flocculated algae can settle out of solution by gravity with or without magnetic flocculation. This process can produce less sludge in the flocculation process.

Removal of Magnetite Residues from Settled Supernatant

Some embodiments concern methods for recycling and reusing media. Magnetite residues in supernatant were observed after gravity settling under a microscope. Magnesium hydroxide precipitates might be one of the negative factors on the magnetite settling in terms of water removal. Using pH adjustment, for example, particles can be recovered for reuse for example using magnetic capture. In addition, a high gradient magnet filter can be used for scale-up operation and recovery of reusable materials. For example, culture media can be recycled for algae cultivation after the magnetite residues are removed.

Kits

In still further embodiments, kits are contemplated herein. In some embodiments, a kit may include one or more composition and/or concentrator for coagulating a suspension culture. Kits may also include one or more suitable container means, magnetic separating device, fluorescent dyes, pH adjusting agents, one or more flocculant, one or more base solution, one or more other extraction or harvesting agents.

EXAMPLES

The following examples are included to demonstrate certain embodiments presented herein. It should be appreciated by those of skill in the art that the techniques disclosed in the Examples which follow represent techniques discovered to function well in the practices disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope herein Example 1

Feasibility of Magnetic Flocculation for Algae Harvesting

Dispersion of Magnetite Particles in Algae Broth

In one example, algae are attached to magnetite particles for magnetic separation. In order to study the attachment, a light microscope was used to observe the magnetite dispersion in the algal growth media. One hypothesis is that positively charged magnesium hydroxide precipitates could bind with both negatively charged algae and magnetite based on electrostatic attraction. The resulting particles can be captured by a permanent magnet, and then algae are concentrated and separated from the media. FIG. 1 illustrates a possible mechanism of the magnetic flocculation proposed. Magnesium hydroxides flocculate algae at a high pH. Magnetite particles tag algae to generate a magnetic property, where the algae can be manipulated in suspension or otherwise under a magnetic field.

FIG. 2 illustrates the microscopic images of magnetite dispersion in the algae broth in absence of a magnet. Magnetite particles were attached with flocculated algae at pH 10.3 observed in these images. Magnetite contents increased from 2.0% (w/v) (FIG. 2A) through 10.3% (w/v) (FIG. 2D). It is observed that more magnetite particles continued to associate with the flocculated algae with increasing magnetite contents from FIG. 2A to FIG. 2D. These observations verified that the algae were capable of being tagged with magnetic particles, indicating that the algal surfaces were modified by magnetic particles. The magnetic algae could be physically moved under a magnetic field. This magnetic modification provides one basis of magnetic separation of use in algae harvesting.

Algae Harvesting Using Magnetic Separation

Figures 3A, 3B, 3C:
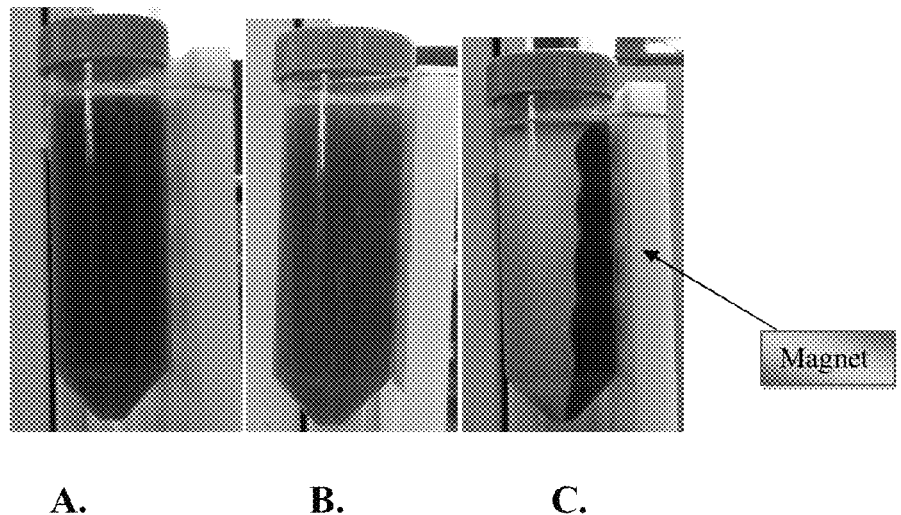
FIGS. 3A-3C represents images of magnetic separation of algae from a solution.

FIGS. 3A-3C illustrates photos of three samples with a permanent magnet applied. FIG. 3A demonstrates the raw algal broth at pH 7.4 in absence of magnetite. There is no significant change in this raw sample as magnesium hydroxide precipitates are not formed at this pH. After increasing pH to 10.4 in FIG. 3B, the sample turned into somewhat turbid, suggesting formation of magnesium hydroxide precipitates. In this example, the magnet did not have a significant influence on this sample likely due to absence of magnetite particles. In FIG. 3C, most of green algae with magnetite were captured by the magnet in presence of the magnetite. Green color in solution was almost disappeared as algae were moved on the tube wall with the magnetite. The supernatant can be easily decanted when holding the magnet, resulting in the concentrated algae obtained. This result demonstrated that the algae were tagged with the magnetite and then were able to be harvested by the magnet.

It is noted that the formation of positively charged magnesium hydroxide precipitates may be required in certain magnetic harvesting methods for algae. Both algae and magnetite are associated with the magnesium hydroxides based on electrostatic attraction, confirming the previous hypothesis. See FIGS. 3A-3C.

(a) Algae broth (pH 7.4) in absence of magnetite
(b) Algae broth (pH 10.4) in absence of magnetite
(c) Algae broth (pH 10.4) in presence of magnetite (1.8% w/v)

Verification of Formation of Magnesium Hydroxide Precipitates

Figures 4A, 4B:
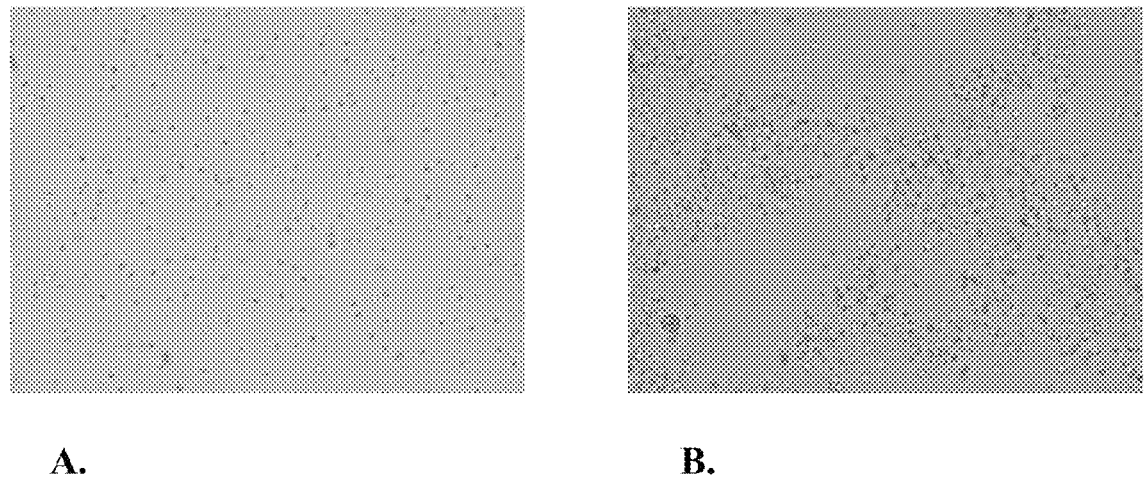
FIGS. 4A-4B represents microscopic images of raw algae before and after flocculation.

Algae were flocculated at pH 10.4 shown in FIG. 2 above. FIGS. 4A and 4B represent the microscopic images of raw algae before and after flocculation. The algae did flocculate at pH 10.4 (FIG. 4B), comparing with separated algal cells at pH 7.7 (FIG. 4A). (A) represents Raw Algae (pH 7.7); (B) Raw Algae (pH 10.4).

Figure 6A:
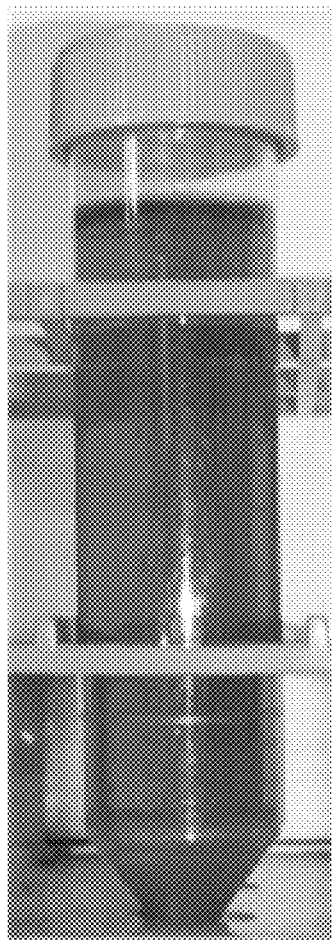
FIGS. 6A-6B illustrate photos of dye indicator in a sample for formation of positive charged precipitates.
Figure 6B:
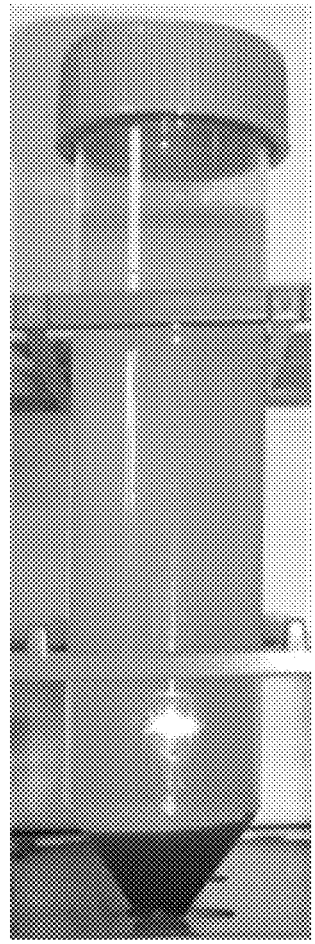

In order to further confirm the formation of positive charged precipitates that activates the flocculation, a method was developed using an anionic dye as an indication. A procedure of this dye indicator is presented as a schematic in FIG. 5. At first, raw algae were removed by centrifugation at initial pH 7.4 where magnesium ions are still dissolved in the supernatant. The pH of supernatant was increased to a higher level (e.g. 9.5 to 10.5) by adding a small amount of base (10.0 mol/L of sodium hydroxide solution). The supernatant turned turbid, suggesting formation of precipitates. In order to verify charge type of the precipitates, a water-soluble dye was added at a low concentration of 47 mg/L. The sample color turned to strong blue of the dye color. The negative charged dye should bind to the precipitates if the precipitates carry positive charges because of electrostatic attraction. The sample was centrifuged again. Blue precipitates should be observed in bottom of the centrifuge tube if this hypothesis is correct. Otherwise, the dye should be still dissolved in solution and the solution remains blue dye color. FIG. 6 illustrates flocculation using a dye indicator with and without pH adjustment. Color difference is apparent before and after pH adjustment. Strong blue color in FIG. 6A was observed at initial pH 7.4. Precipitates of magnesium hydroxides did not form at this pH, where the dye was still dissolved in solution with its color. In contrast, blue precipitates in the bottom and colorless supernatant in FIG. 6B were observed after pH adjustment to 10.4. The results from FIGS. 6A and 6B confirm that the positive charged precipitates were formed at high pH 10.4. FIGS. 6A and 6B illustrates photos of dye indicator for formation of positive charged precipitates, (A) Dye (47 mg/L) in supernatant (pH=7.4), centrifuged again at 5,000 rpm for 10 min. and (B) Dye (47 mg/L) in supernatant (pH=10.4), centrifuged again at 5,000 rpm for 10 min.

Algae Harvesting Through Magnetic Separation

In one exemplary method, algal cells were directly captured by a permanent magnet in presence of particles of iron and magnetite at different sizes and contents. In these examples, magnetite appeared to perform better than the irons tested. Here, three types of magnets were tested where they were all capable of capturing algae-magnetite flocs from medium. In these experiment configurations, a high recovery of algae (about 97%) was obtained using a magnetite content of about 2.0% (w/v) and a strong plate magnet. In one method, a magnetic belt conveyor was suggested for algae harvesting in a continuous mode. An enhanced magnetic plate using strong magnetic discs capable of use in a belt conveyor was constructed and tested. This resulted in about 91% of the algae captured from medium. It is possible that suspension microorganisms can be captured from a continuous mode for a high percent recovery of algae and high percent removal of medium. These methods could lead to magnetic separation for suspension cultures like algae by quick harvesting using low energy input to reduce time and cost. These examples do not use a settling step for harvesting.

Example 2

Effects of pH on the Magnetic Flocculation

Figure 7:
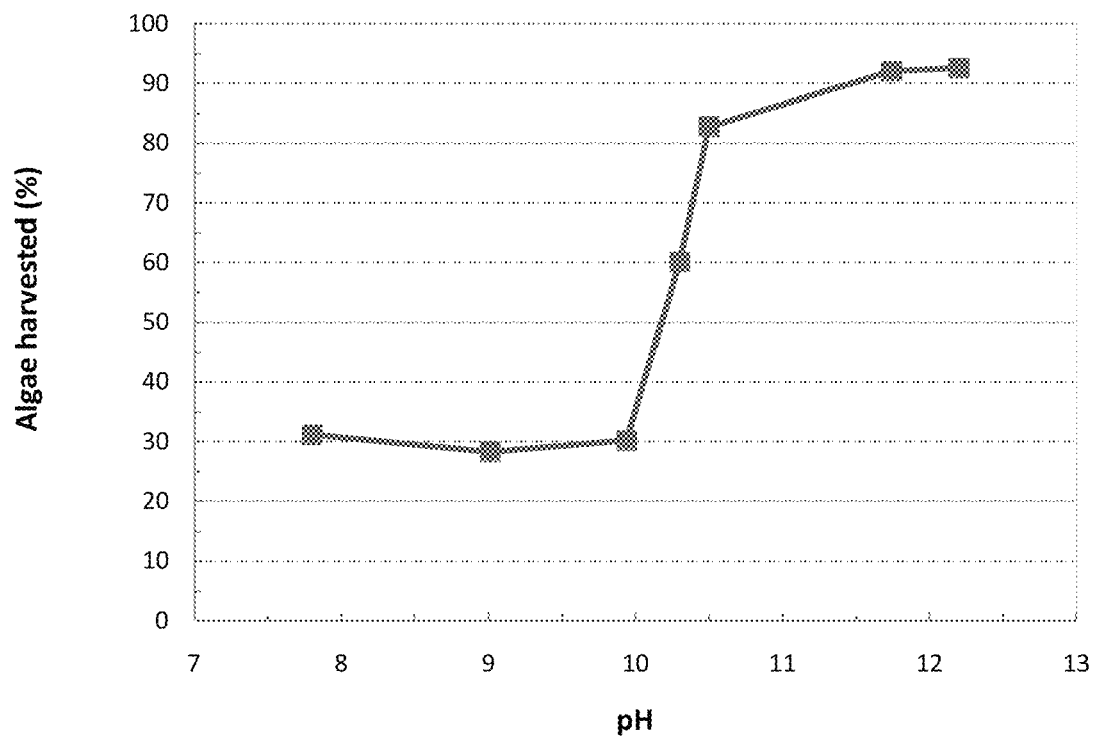
FIG. 7 represents effects of solution pH on algae harvesting.

As discussed above, pH is one of the key factors in formation of magnesium hydroxides and then further magnetic flocculation. Effect of solution pH on the algae harvesting efficiency is illustrated in FIG. 7. Harvesting efficiency is defined as the difference of algae densities between raw algae broth and the separated supernatant over the algae density of raw broth. As expected, the solution pH had a significant influence on the algae harvesting efficiency. When a solution pH was below 10.0, algae harvesting was about 30%, suggesting that some of the magnesium hydroxides did not form. Once adjusted to pH 10.0, algae harvesting efficiency increased and reached a maximum value of 92% at pH 11.7. Over this pH change, algae harvesting did not exhibit a significant change. Comparing the pH profile of magnesium hydroxides, the formation of magnesium hydroxides occurred in pH range of 10.0 to 11.7 in FIG. 7 in this study. The results from FIG. 7 demonstrated that magnesium hydroxide precipitates play a key role in the algae harvesting. In addition, high harvesting efficiency (about 92%) was obtained using this magnetic flocculation under these conditions.

In one example, magnesium was added to a culture to a final concentration of about 2,000 mg/L and the pH was adjusted to about 9.5. In this example, there is support that harvesting pH can be dependent of the concentration of heavy agent provided to the culture and this example led to a harvesting recovery of about 99% (Table 1). Therefore, in certain exemplary methods, base addition and pH adjustment to a more basic pH may not be needed if the precipitating agent (e.g. magnesium) is provided at higher concentrations. Therefore, this could eliminate or significantly reduce costs related to supplementing the media with base for pH adjustment.

TABLE 1

Magnetic flocculation at pH 9.5 at various levels of magnesium concentrations

| Sample | DW25-#1 | DW25-#2 | DW25-#3 | DW25-#4 |
|---|---|---|---|---|
| Magnesium added (mg/L) | 498.0 | 994.7 | 1,504.9 | 2,032.7 |
| $Fe_3O_4$ (% w/v) | 1.0 | 1.0 | 1.0 | 1.0 |
| Algae recovery* (%) | 27.6 | 38.5 | 91.0 | 99.8 |

*Algae recovery is defined as percentage of difference of algae densities between raw algae broth and supernatant to algae density in raw algae broth In certain examples, a high pH (e.g. >9) appears to be needed for magnesium-based harvesting technology because of formation of magnesium hydroxides. It is noted that the pH increase can vary in expense output due in part to different bases added to a solution. Therefore, three different bases, sodium hydroxide (NaOH), calcium hydroxide ($Ca(OH)_2$), and ammonium hydroxide ($NH_4OH$), were investigated in this study.

Sodium Hydroxide Addition

Figure 8:
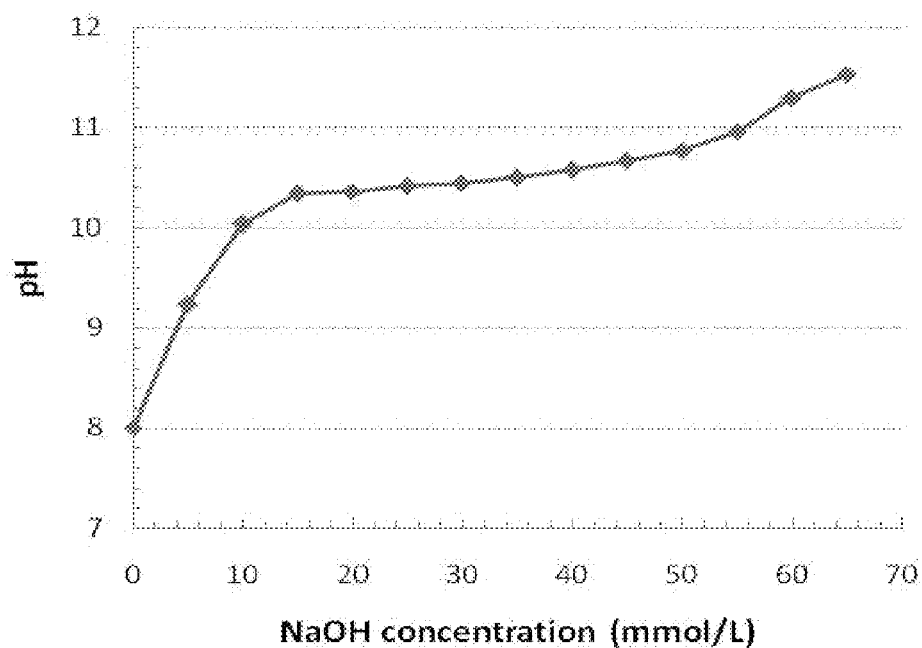
FIG. 8 represents effects of solution pH as a function of NaOH concentration.

Sodium hydroxide is a strong base and is soluble in water. Sodium hydroxide solution at high concentration (e.g. 10.0 mol/L) was added to algae broth for an increase in pH. FIG. 8 illustrates a plot of solution pH as a function of NaOH concentrations. At pH below 10.1, the solution pH appeared to increase linearly with increase of NaOH concentrations, suggesting that NaOH addition was directly proportional to the increase in solution pH. The solution pHs between 10.3 to 11.0 only slightly increased with NaOH addition. As discussed above, magnesium hydroxides are precipitated at this pH range. So the NaOH added was consumed by precipitation of magnesium hydroxides, resulting in slow increase of pH. After this point, the solution pH increased sharply again as the magnesium ions was consumed completely.

Ca(OH)$_2$ Addition

Figure 9:
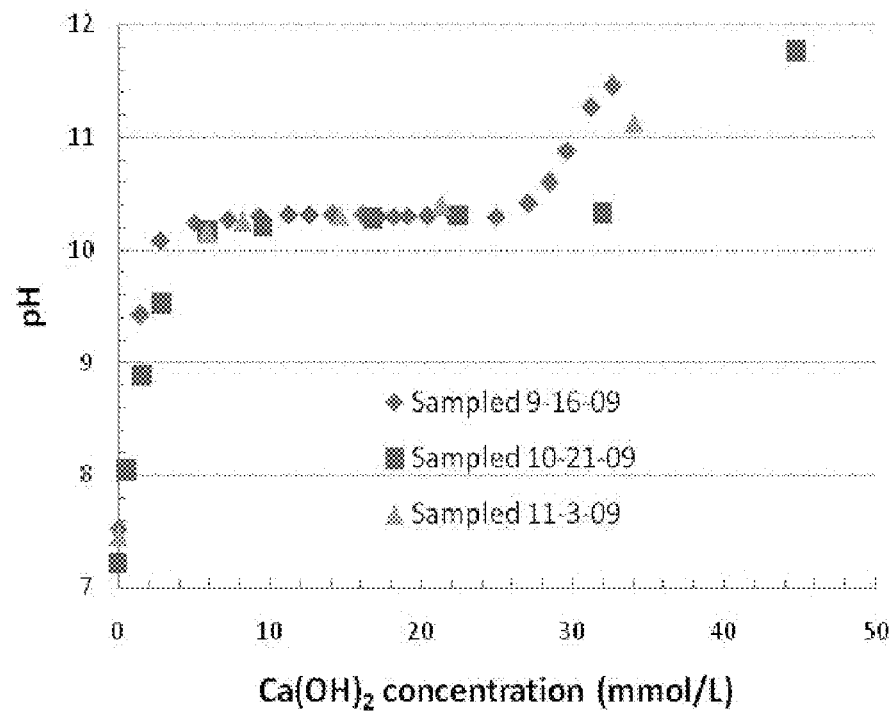
FIG. 9 represents an exemplary plot of solution pH as a function of $Ca(OH)_2$ concentration.

Unlike sodium hydroxide, calcium hydroxides (Ca(OH)$_2$) is a relatively inexpensive source of base reagent, commonly used to increase pH in wastewater treatment. Calcium hydroxide has low solubility in water at pH above 10. Solid calcium hydroxide was directly added in the algae broth in this study due to this property. The results from the calcium hydroxide addition are illustrated in FIG. 9. As observed, a similar trend was observed as that of sodium hydroxides. Three algae samples were tested with algal densities varied from 1.9-3.4 g/L. There is no significant difference found, indicating that solution property (e.g. magnesium concentrations), not algal densities, played a key role in the pH changes in addition of base. FIG. 9 illustrates *N. salina* of 1.9 g/L; *N. salina* of 3.4 g/L; and *N. salina* of 2.1 g/L.

NH$_4$OH Addition

Figure 10:
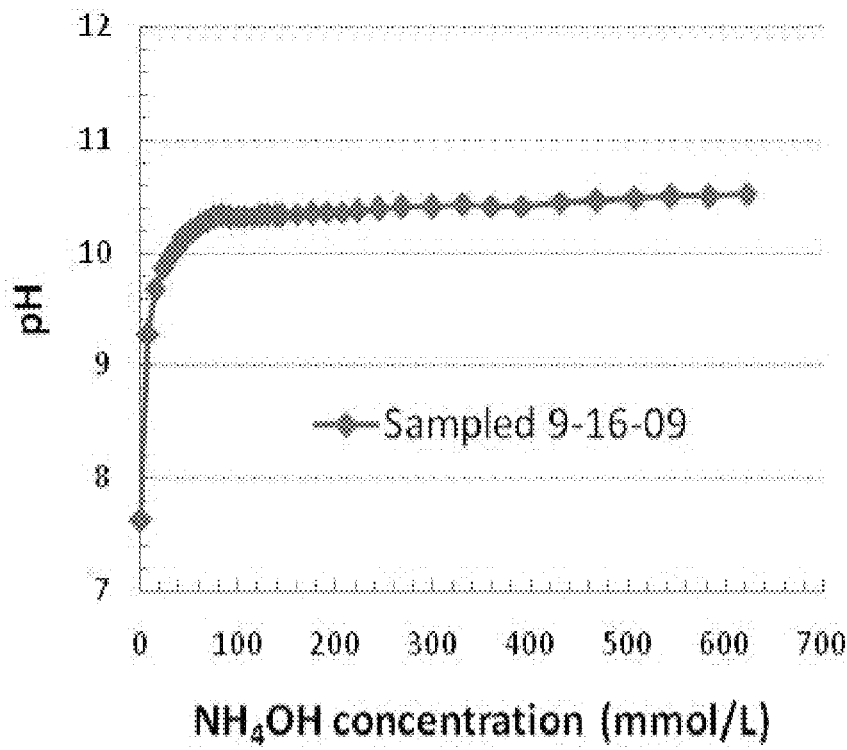
FIG. 10 represents an exemplary plot of solution pH as a function of $NH_4OH$ concentration.

Another base tested was a weak ammonium hydroxide (NH$_4$OH). Similar to NaOH addition, a concentrated ammonium hydroxide solution (28-30% wt) was used for the pH adjustment. FIG. 10 illustrates that the solution pH as a function of NH$_4$OH concentrations. Comparing to NaOH and Ca(OH)$_2$, high NH$_4$OH concentration of approximate 50 mmol/L is required to reach pH 10.2 and then increased slowly. For example, solution pH was 10.3 at NH$_4$OH concentration of 150 mmol/L. Also, solution pH was still 10.5 when the NH$_4$OH concentration reached at 620 mmol/L. The results suggested that there was a low efficiency of pH increase with NH$_4$OH addition than that of NaOH and Ca(OH)$_2$ because NH$_4$OH is a weak base.

Nitrogen Stripping

Rather than base addition, inert gas (e.g. nitrogen) stripping was also used to increase pH. Although inert gas does not have any chemical reaction when it passes through solution, dissolved CO$_2$ in solution is stripped out of solution, resulting in pH increase. In active cultures, CO$_2$ will also be consumed by photosynthetically active algae, again resulting in pH increase. Nitrogen gas stripping was studied in lab tests, where the nitrogen gas from a gas tank passed through the algae broth (150 mL). The solution pH increased from 7.3 to 9.5 with nitrogen stripping, indicating that inert gas stripping can be used to increase pH. It is noted that pH of above 10 was not observed in this experiment, even after 420 minutes exposure. This may be due to the algae being tested in lab was not very activated for consuming the dissolved CO$_2$ in the media. A pH of above 10 was obtained with air stripping when algae were grown outside under sunlight. So inert gas (e.g. air) stripping might provide a cost-effective way to increase pH as it does not introduce any chemicals into media, which might not introduce any negative influence on media recycle for algae cultivation.

Example 3

Effect of Magnetite Contents on the Magnetic Flocculation

Figure 11A:
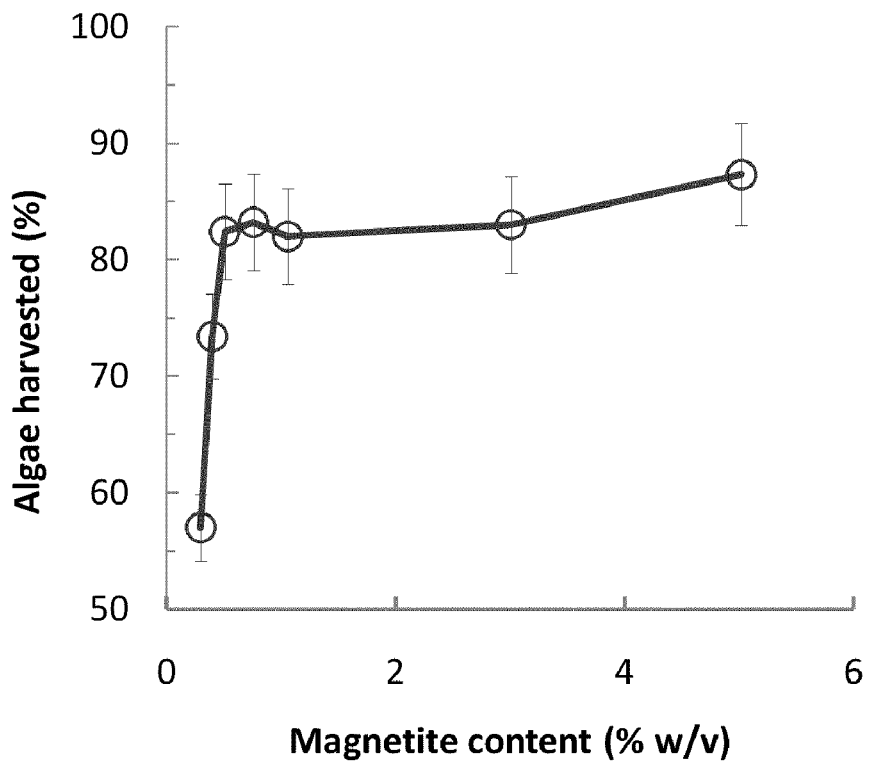
FIGS. 11A and 11B represent effect of magnetite content on algae harvesting.
Figure 11B:
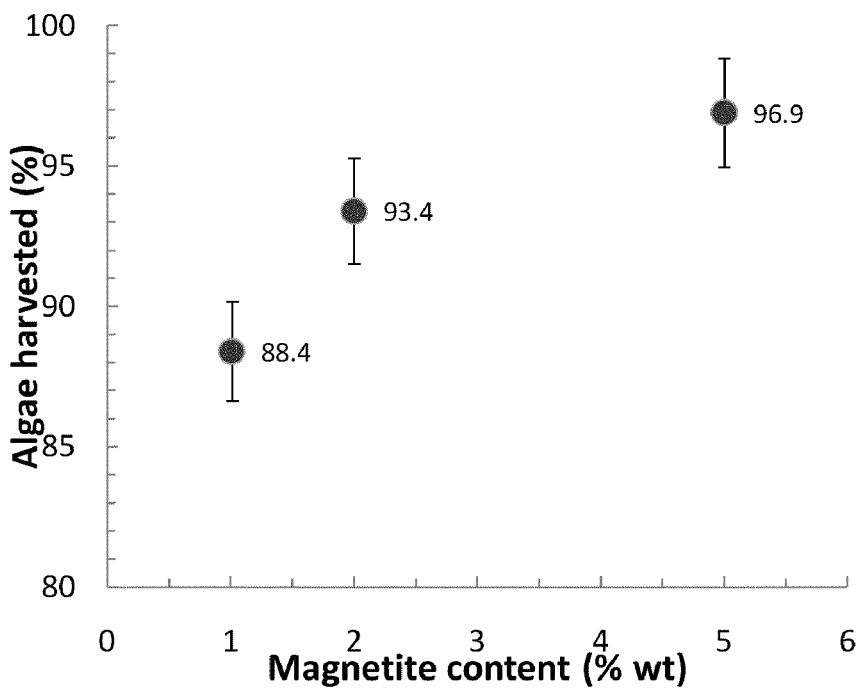

After algal surfaces become positive charge in presence of magnesium hydroxides, negative magnetite particles will attach to the algae due to electrostatic attraction. Magnetite contents affect algae harvesting performance. Effect of the magnetite contents on the algae harvesting were shown in FIGS. 11A and 11B. As can be seen in FIG. 11A, the magnetite content affected significantly the harvesting efficiency. The harvesting of algae (*N. oculata* of 1.7 g/L) decreased sharply when the magnetite content was below 0.5% (w/v), suggesting that magnetite particles were not sufficiently prevalent to attach entire algal cells in the media. As magnetite content increased, the algae harvesting increased slightly from 82% to 87% as the magnetite content increased from 0.5% to 5.0% (w/v). So magnetite content should be higher than 0.5% (w/v) in order to obtain high harvesting performance. Similar results were obtained using *N. salina* of 3.4 g/L shown in FIG. 11B, confirming the influence of magnetite contents. High efficiency of harvesting (96.9%) obtained could be due in part to high cell density of 3.4 g/L used in this test.

Recovery of Concentrated Algae and Magnetite Particles

After the algae harvesting, the algae-magnetite particles can be separated to obtain the concentrated algae and the magnetite particles. One method is to decrease solution pH below the pH level at which dissolved magnesium hydroxide precipitates. Here, magnetite particles were separated from the media by a magnet as electrostatic repulsion occurred between the algae and the magnetite. FIG. 12 illustrates separation of the concentrated algae and the magnetite at lower pH 6.6. The magnetite was captured on the tube wall by a magnet and the concentrated algae left in the solutions in bottom in the sample. The observation demonstrated that the algae were concentrated by the magnetic flocculation method through pH adjustment.

In order to investigate potential magnetite remaining in the concentrated algae, light microscopy was used to observe the algae before and after the magnetic recovery. FIGS. 13A-13B illustrate microscopic images of before and after the magnetite removal in the sample. In this Sample, pH was decreased from 10.5 (FIG. 13A) to pH 6.6 (FIG. 13B). A significant change was observed. In the higher pH, the algae were flocculated with binding to magnetite. In the lower pH of 6.6, the algae were separated without the flocculation and most of the magnetite particles were removed (few magnetite particles were found in this sample). The observations from FIG. 13 demonstrated that the magnetite particles were separated by decreasing pH and the concentrated algae were obtained. So it is suggested that recovered pH could be about 6.6 in order to get concentrated algal cells essentially free of magnetite.

Regeneration and Reuse of the Magnetite Particles

Figure 14:
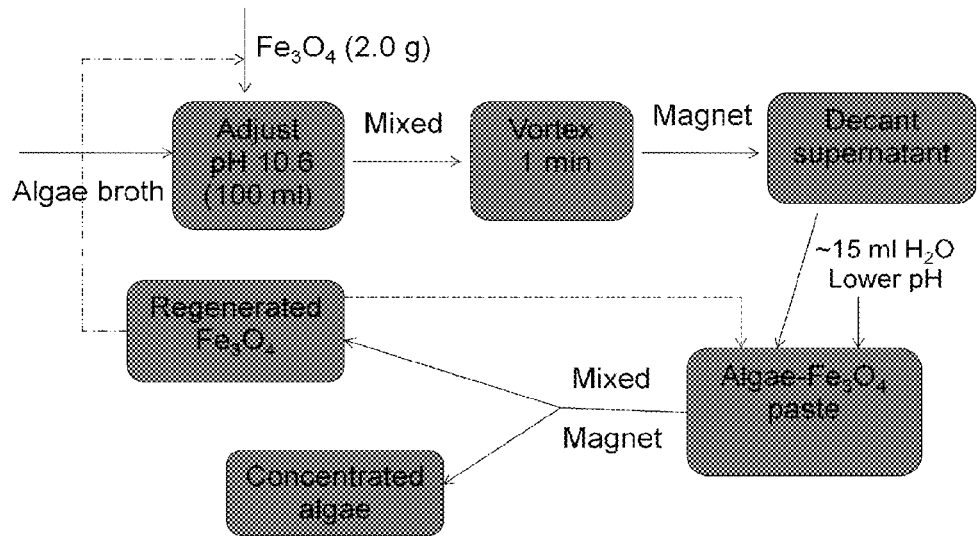
FIG. 14 represents an exemplary experimental protocol of regeneration and reuse of magnetite particles.

It may be necessary to regenerate and reuse the magnetite particles in order to reduce the particle cost. A set of experiments in batch was designed to test whether the magnetite particles can be reused. The experimental protocol is presented in the schematic of FIG. 14. The pH of algae broth (100 mL) was adjusted to 10.6 and dry magnetite particles (2.0 g) as 2.0% (w/v) were added into the first broth. The sample was mixed by a vortex mixer for one minute and the supernatant was decanted while applying a magnet. Approximately 15 mL of water were added into the algae-Fe$_3$O$_4$ paste and pH was lowered to 6.5-8.1. The magnetite and concentrated algae were separated by holding the magnet. The resultant magnetite particles were reused by adding into a new batch of algae broth. In Batch #8, the resultant magnetite before reuse was regenerated by an additional step of water washing, lowering pH and recovering by use of the magnet.

Experimental conditions in nine batches were presented in the Table 2. The wet magnetite particles were reused in all experiments except the first. Harvesting pHs were at 10.6 except that in Batch #5.

TABLE 2

Nine experiments of the regeneration and reuse of magnetite

| Sample batch | Magnetite | Harvested pH | Regenerated pH |
|---|---|---|---|
| #1 | dry | 10.6 | |
| #2* | wet | 10.6 | 8.1 |
| #3 | wet | 10.6 | 6.8 |
| #4 | wet | 10.6 | 7 |
| #5 | wet | 10.3 | 6.5 |
| #6 | wet | 10.6 | 6.6 |
| #7 | wet | 10.6 | 6.5 |
| #8 | wet | 10.6 | 6.5, 7.9 |
| #9 | wet | 10.6 | |

*Continuous harvesting without removal of attached algae
(*N. oculata* of 1.9 g/L, initial pH = 7.4)

Figure 15:
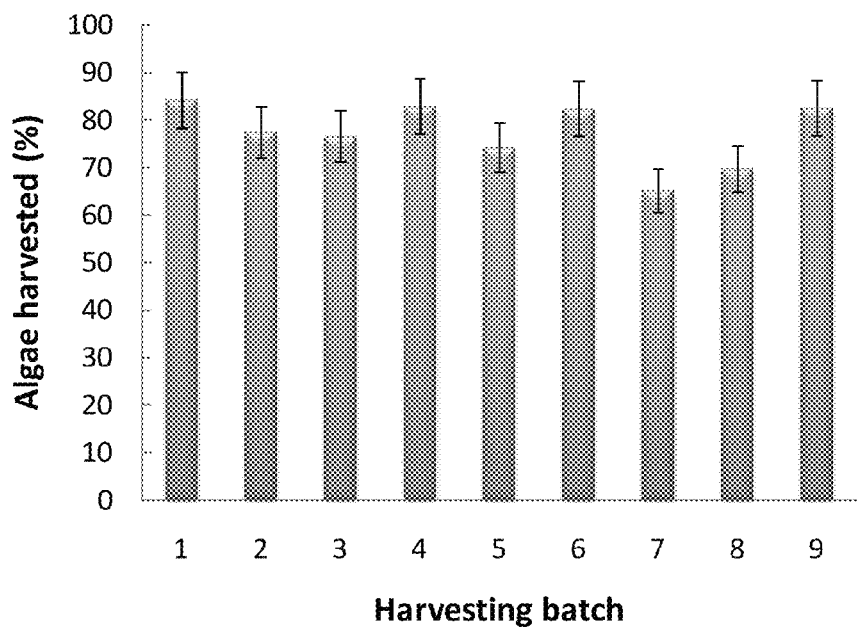
FIG. 15 illustrates a bar graph representing harvesting suspension cultures with reusable magnetite.

The results of algae harvesting using reusable magnetite were shown in FIG. 15. In general, six of nine batches (#1, #2, #3, #4, #6, and #8) did vary slightly on harvesting efficiencies (77-84%). Slightly lower harvesting (74%) in Batch #5 was obtained as slight lower pH 10.3 of harvesting was used in comparison with 10.6 in other batches. However, lower harvesting efficiency of 65% in Batch #7 and 70% in Batch #8 were obtained, suggesting that the wet magnetite particles needed to be regenerated after the first six batches of harvesting. The magnetite particles were washed twice in Batch #8 and the harvesting efficiency of 83% was achieved in Batch #9. The results from FIG. 15 demonstrate that the magnetite particles tested can be reused without a significant loss in harvesting efficiency after simple water washing was used for regeneration.

Example 4

Enhancement of Sedimentation in Presence of Inorganic Particles

Alternative to the magnetic separation, gravity sedimentation can be an inexpensive and reliable process. The flocculated algae tied with magnetite could settle to the bottom if the algae density is higher than that of growth media. Certainly, the higher density of magnetite and algae will lead to higher efficiency of sedimentation in term of shorter time and less volume of the concentrated algae. The density of magnetite and algae associates with physical properties of the magnetite used. Table 3 represents physical properties and the particle size distribution of the magnetite particles (e.g. Pirox 200) used in this study. The specific gravity of the particles is 5.23 g/cm$^3$, which tends to gravity sedimentation. The particle sizes are smaller than 4.0 microns in 90% of the particles and smaller than 2.0 microns in 50% of the particles. Particles of very small sizes do not tend to sedimentation although they provide more specific surface area (3.0 m$^2$/g) for the algae attachment.

TABLE 3

Physical properties of magnetite powder (Fe$_3$O$_4$) from Pirox 200

| | |
|---|---|
| Bulk Density | 737 kg/m$^3$ |
| Specific Gravity | 5.23 g/cm$^3$ |
| Specific Surface Area | 3.0 m$^2$/g |
| Numeric Particle Size | |
| D50 | 2.0 μm |
| D90 | 4.0 μm |

Figure 16:
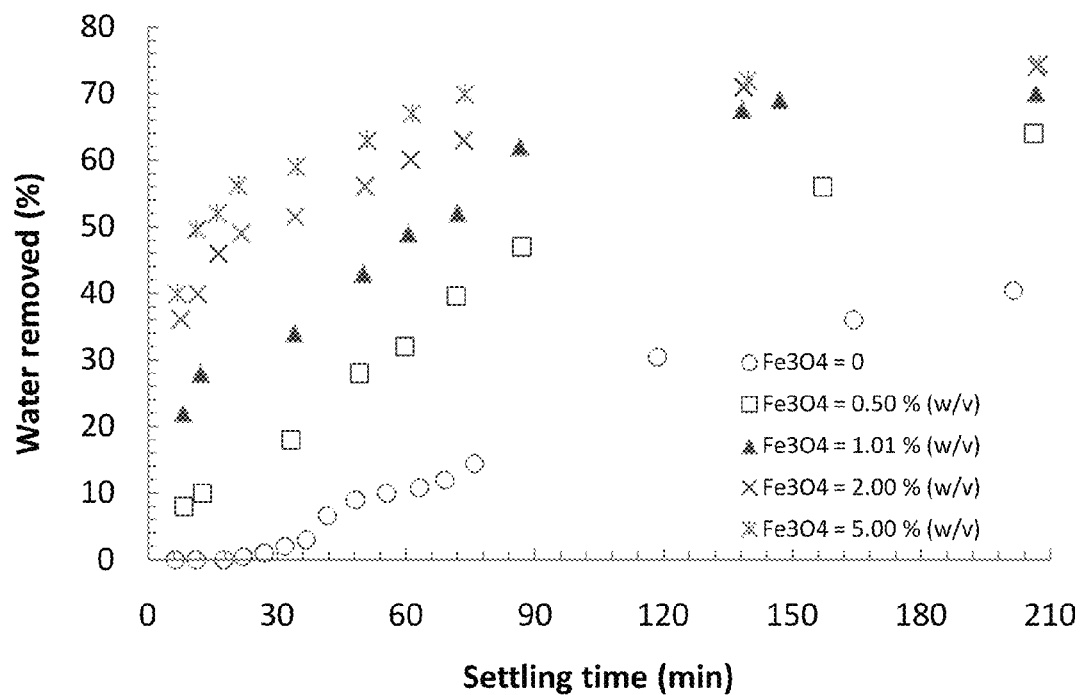
FIG. 16 represents effects of magnetite contents on the algae sedimentation by gravity.

In addition, a ratio of magnetite to algae (or content of magnetite for a specific density of algae broth) will also affect the algal sedimentation. FIG. 16 represents effects of magnetite contents on the algae sedimentation by gravity. The water removed is defined as the separated supernatant volume over the total volume of raw algal broth. The water removed was significantly increased with increasing content of magnetite from 0 to 5.0% (w/v). The settling performance has significantly changed when the magnetite contents were below 2% (w/v). After a range of 2% to 5%, there was only a slight difference, for time (e.g. >140 minute). Settling performance was significantly improved with time. The highest amount of water removed, about 74%, was obtained when the magnetite contact was higher than 2.0% (w/v) at 208 minutes. FIG. 16 represents sedimentation by gravity in presence of the magnetite (*N. oculata* of 1.7 g/L, settling pH 10.6).

Figure 17:
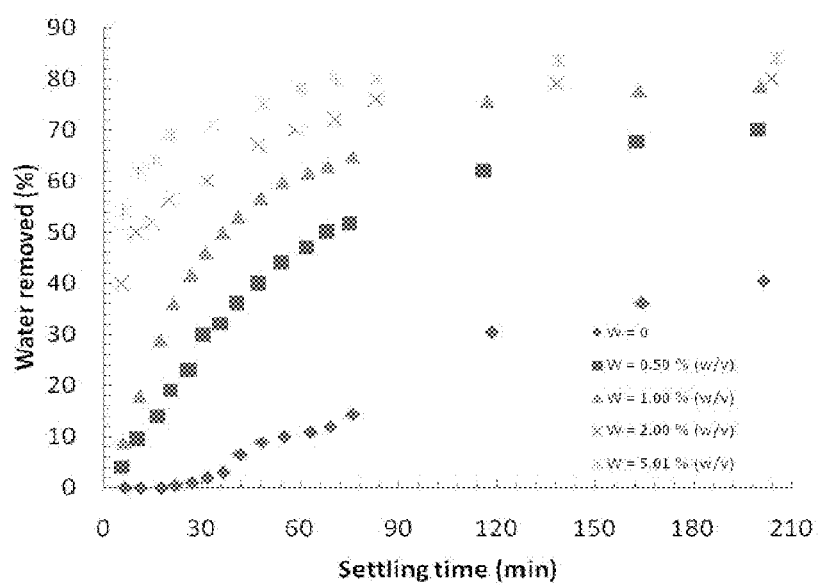
FIG. 17 represents sedimentation performance of suspension cultures using tungsten.

In order to investigate particle density on influence of the settling performance, another high density material of non-magnetic metal particles was selected, tungsten (W). Tungsten in this test has a density of 19.3 g/cm$^3$ with a particle size of about 0.6-1 μm. The sedimentation performance varied as shown in FIG. 17. Similar results compared to the magnetite sedimentation profile were obtained with the use of tungsten. The highest water removal was 84% in this study when the tungsten content was 5.0% (w/v) at 206 minutes of the settling time, which was greater than that of 74% using the magnetite demonstrated in FIG. 16. Sedimentation by gravity in presence of the tungsten (*N. oculata* of 1.7 g/L, settling pH 10.6) is also represented here.

Figure 18:
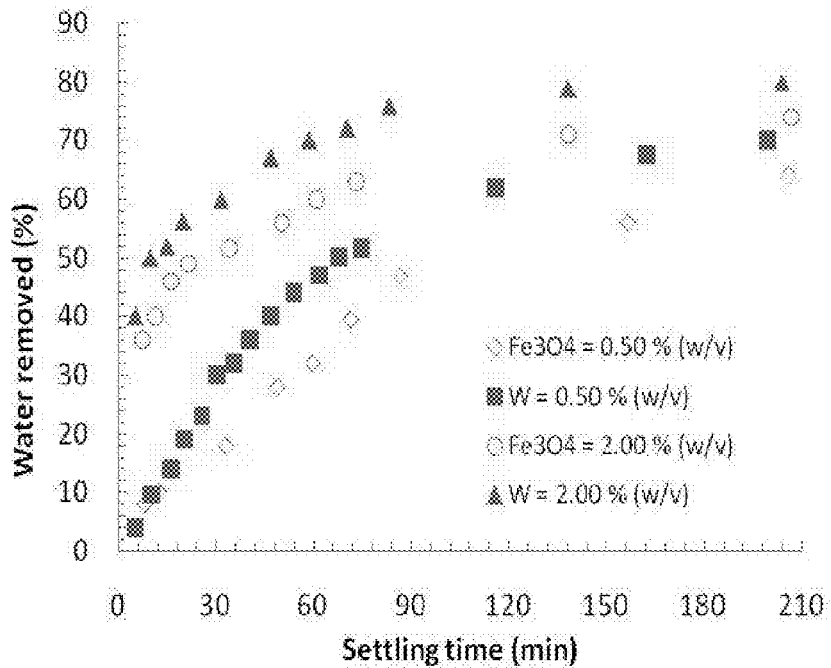
FIG. 18 represents a comparison of magnetite and tungsten on sedimentation by gravity of a suspension culture.

To compare magnetite and tungsten regarding sedimentation, two particle contents (0.5% and 2.0%) were selected. The results are presented in FIG. 18. Higher extent water removal using tungsten was shown than that using magnetite in both concentrations of particles, demonstrating that tungsten has superior performance of sedimentation compared to magnetite. The results confirmed that particle density plays a role in the sedimentation when even lower particle size of tungsten (0.6-1 μm) was used in comparison to the magnetite in bigger sizes (see Table 2). FIG. 18 represents a comparison of magnetite and tungsten on sedimentation by gravity (*N. oculata* of 1.7 g/L, settling pH 10.6).

Effect of Particle Size on Algae Settling by Gravity
Enhancement of Sedimentation in the Presence of Inorganic Particles In other exemplary methods, different particle sizes were tested for their effects on sedimentation of suspension cultures described herein. For example, particles of iron and silica in three different sizes ranging from several micrometers to hundred micrometers were selected as model systems in an algal model. Both iron and silica can enhance the algae settling within certain limitations of particle sizes. In these examples, very low dry mass of about 0.04 g/L in supernatant was obtained in comparison to raw dry mass of 3.7 g/L. Iron particles in three different sizes were tested in order to determine size limitation. For algae settling in presence of iron particles, particle sizes in 6-9 μm and about 44 μm demonstrated clear settling at about 60 min. The dry masses in the supernatants were 0.02 g/L and 0.04 g/L, respectively, indicating that about 99% of algae were settled in the slurry in comparison to the dry mass of 3.7 g/L in raw algae broth. It was observed that no significant difference in settling was documented for these test sizes even though one used about 44 μm particles, much bigger than the other at 6-9 μm. Iron particles in size of 10-40 mesh (420-2,000 μm) did not appear to significantly enhance the algae settling in these examples. Silica in size of 50-70 mesh (297-210 μm) also did not seem to enhance settling. These larger particles did not attach to algae when they mixed with algae, likely because they settled alone by gravity without associating with algae. Of these particles tested, iron material may be one good candidate for algae harvesting because of its magnetic properties and inexpensive material cost. It is contemplated that the particle size can be about 1 μm to about 100 μm, in order to enhance settling of a suspension culture.

TABLE 4

Densities and sizes of particles tested

| Particle | Density (g/ml) | Size |
|---|---|---|
| Iron | 7.86 | (1) 6-9 μm |
| | | (2) ~325 mesh (~44 μm) |
| | | (3) 10-40 mesh (2,000-420 μm) |
| Silica | 2.6 | (1) 0.5-10 μm (80% between 1-5 μm) |
| | | (2) <230 mesh (<63 μm) |
| | | (3) 50-70 mesh (297-210 μm) |
| Tungsten | 19.3 | (1) 0.6-1 μm |
| Magnetite | 4.8-5.2 | (1) <5 μm |
| | | (2) <10 μm (50% less than 2 μm, 90% less than 4 μm) |

Example 5

Process Design and Continuous Harvesting Algae

Process Design

Figure 19:
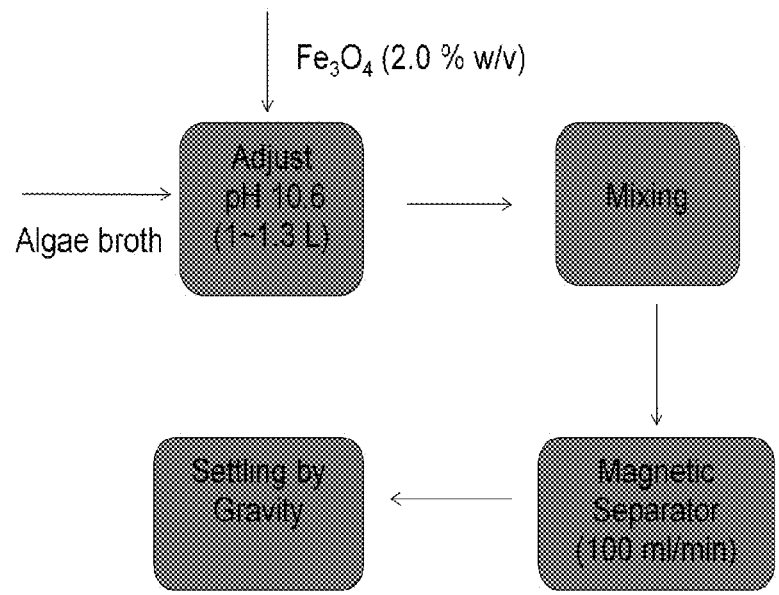
FIG. 19 represents experimental protocols of magnetic harvesting in presence of magnetite.

In one exemplary experiment, a new process was developed based on the magnetic flocculation. A schematic of flow chart of the harvesting process is shown in FIG. 19. Algae broth will be sent to Tank #1 for increasing pH and adding iron oxides. Mixing in retention time of 5-10 minutes is required to make uniform dispersion of iron oxides in the Tank #1 and the mixed algae will pass through a Magnetic Separator. The magnetite and attached algae will be settled by gravity in a Settler #1 in retention time of 15-60 minutes, aiming at 75-90% (v/v) of supernatant returning to the algae cultivation system. The remaining 10-25% (v/v) flocculated algae-iron oxides will be transferred to Tank #2 for pH decrease. The resulting algae will be sent to Settler #2. In another example, the recovered iron oxides might need an additional step of water washing for regeneration and then will be sent back to Tank #1 for reuse. The resultant algae concentrates will be sent to further processing for lipid extraction.

It is noted that the general magnetic separator used for separation is not limited to the particular type of Magnetic Separator used here. It could be equipment which provides a magnetic field for enhancement of algae sedimentation. Also, the Magnetic Separator may be placed next to the Settler #1. In addition, the Magnetic Separator could be removed.

Example 6

Continuous Harvesting Algae

Role of Magnetite Particles in the Magnetic Harvesting

Figure 20:
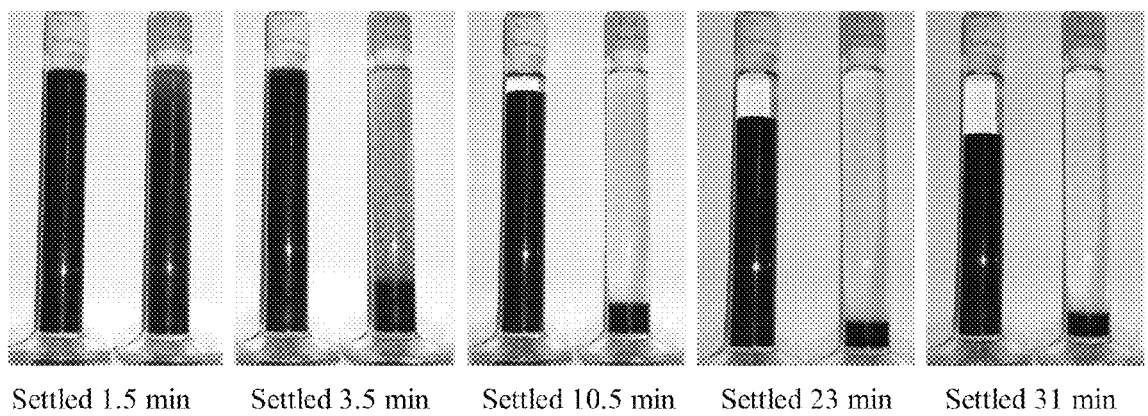
FIG. 20 represents photographs of enhancement of suspension culture settling by a magnetic field.

In order to examine influence of magnetite particles, another experiment using a magnetic separator was designed as illustrated in FIG. 20. Algae broth (*N. salina* of 3.44 g/L, 1.0-1.3 liter) was mixed by mechanical stirring at about 1,000 rpm for about 5 min in presence of magnetite (2.0% w/v) or in absence of magnetite. The algae broths were passed through a Magnetic Separator with permanent magnets (Model PQ-2, S. G. Frantz Co. Inc.) at a flow rate of 100 ml/L. The resultant algae were settled by gravity. Three tests were conducted under experimental conditions presented in Table 5. Four samples were taken for dry mass determination for evaluation of harvesting efficiency. Each example was collected in Test #1 and Test #2 after the tests were completed. Two samples were taken at 2.5 and 4.0 minutes after the algae were passed through the Magnetic Separator.

TABLE 5

Three experiments with the Magnetic Separator in presence or absence of magnetite

| Test | pH | Magnetite (% w/v) | Sampled time (min) | Dry mass (g/L)[b] | Algae harvesting (%) |
|---|---|---|---|---|---|
| #1 | 7.3 | 0 | finished[a] | 3.12 | 9.3 |
| #2 | 10.6 | 0 | finished[a] | 2.81 | 18.3 |
| #3 | 10.6 | 2.5 | 2.5 | 0.10 | 97.1 |
| | | | 4.0 | 0.08 | 97.8 |

[a]The samples were taken after the experiments were completed.
[b]All samples were settled about 30 minutes and then dry mass in the supernatants were determined.

In both Test #1 and Test #2, a significant color change was not observed, after the (bright green) algae were passed through the Magnetic Separator. This observation suggested that the Magnetic Separator did not capture a lot of algae even when the algae were flocculated by magnesium hydroxides at pH 10.6 in Test #2. However, significant color changes were observed in Test #3. Almost colorless effluent was first found at about 2 minutes, indicating that the algae were captured by the Magnetic Separator. This is confirmed by the fact that the captured algae were found inside the Magnetic Separator when the Separator was opened. After running about 2.5 minutes, the algae flowed out the system, indicating that the Separator had reached a capture capacity in this test.

The harvesting results were presented in the Table 5. The day mass of 3.12 g/L in Test #1 was slightly lower than that of raw algae of 3.44 g/L, suggesting that a small amount of algae was adsorbed in the Separator. In addition of the adsorption, the flocculated algae in Test #2 had further slight sedimentation and resulted in lower dry mass of 2.81 g/L. However, sharp reductions in the dry mass (0.10 and 0.08 g/L) were obtained in both samples of Test #3. High algae harvesting efficiency (>97%) was found in Test #3. From the results of three tests, it is concluded that magnetite particles indeed enhanced the algae harvesting using the Magnetic Separator.

Example 7

Enhancement of Algae Sedimentation by Magnetic Separator

Sedimentation of the algae-magnetite flocs is enhanced by a magnetic field. When the broth containing algae-magnetite passes through a magnetic field, the algae-magnetite flocs become magnetized and attached to each other and formed larger flocs. The larger flocs have enough mass to cause them to settle out of the media at a much faster rate than initial algae-magnetite flocs. Experiments were conducted to verify this hypothesis using same procedure in FIG. 20. The only difference was to withdraw one more sample (Separator Influent) without passing the Magnetic Separator in order to compare with the sample (Separator Effluent) which had passed through the Magnetic Separator.

However, the colorful algae flowed out the Magnetic Separator after about 9 minutes. This observation suggested that the Magnetic Separator had reached saturation of the algae capture capacity. Longer time of 8.5 minutes for clear effluent in this test was observed than that (about 2 minutes) of the test (Example 6) discussed previously. There may be lower algae density (e.g. 2.06 g/L) in this test in comparison to the previous test (e.g. 3.44 g/L). The ratio of magnetite to algae density may influence the capture capacity of the Magnetic Separator.

However, the colorful algae flowed out the Magnetic Separator after about 9 minutes. This observation suggested that the Magnetic Separator has reached saturation of the algae capture. Longer time of 8.5 minutes for clear effluent in this test was observed than that (about 2 minutes) of the test discussed previously. There may be lower algae density (e.g. 2.06 g/L) in this test in comparison to the previous test (e.g. 3.44 g/L). The ratio of magnetite to algae density may influence the capture cap of the Magnetic Separator.

100 ml of effluent after 9 minutes was collected to start sedimentation by gravity in comparison to another sample, influent, without passing through the magnetic separator. FIG. 20 illustrates photos of two samples in various settling time. Significant differences were observed between the two samples. The effluent settled much faster than the influent in the time period tested. This observation demonstrated that the magnetic field provided by the Magnetic Separator significantly enhanced the algae sedimentation due to magnetization of the magnetic algae. For example, the effluent separated about 85 ml of supernatant in comparison with about 10 ml of supernatant separated in the influent in 10.5 minutes. About 90 ml of supernatant was separated in the effluent in settling 31 minutes, indicating that about 90% of water can be removed by this system. FIG. 20 represents enhancement of algae settling by a magnetic field. Left sample: influent (marked "No Treatment" (NT)); Right sample: effluent (marked "Treated" (T)).

Figure 21A:
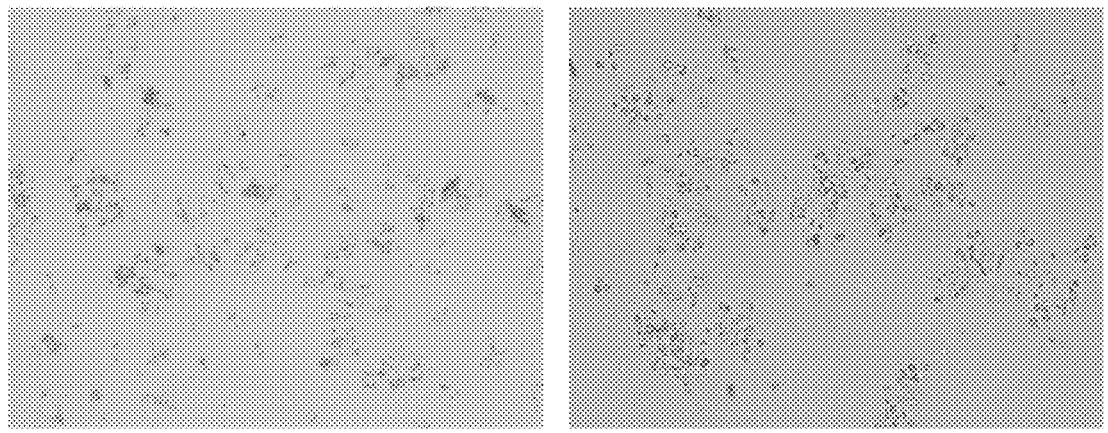
FIGS. 21A-21D represents microscopic images of suspension cultures during the harvesting process.
Figure 21B:
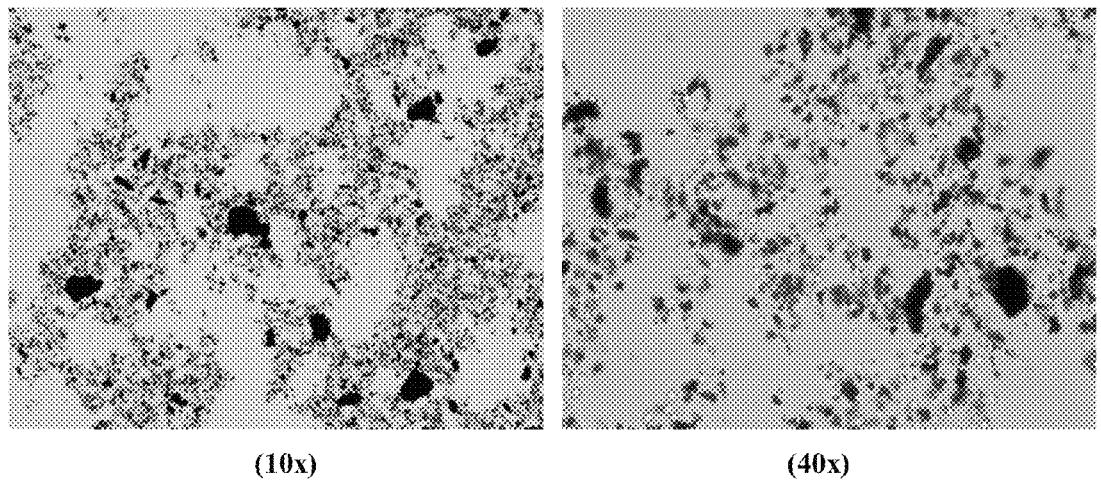
Figure 21C:
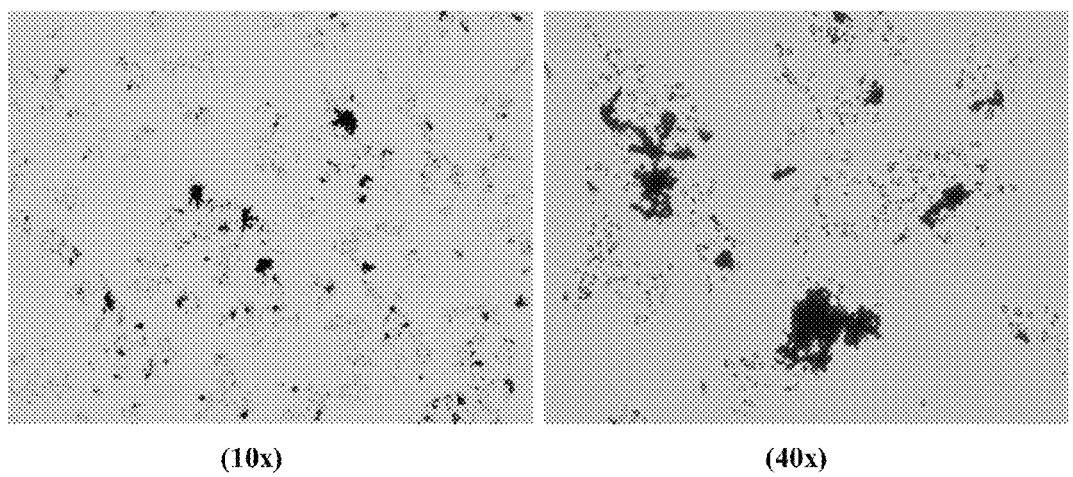
Figure 21D:
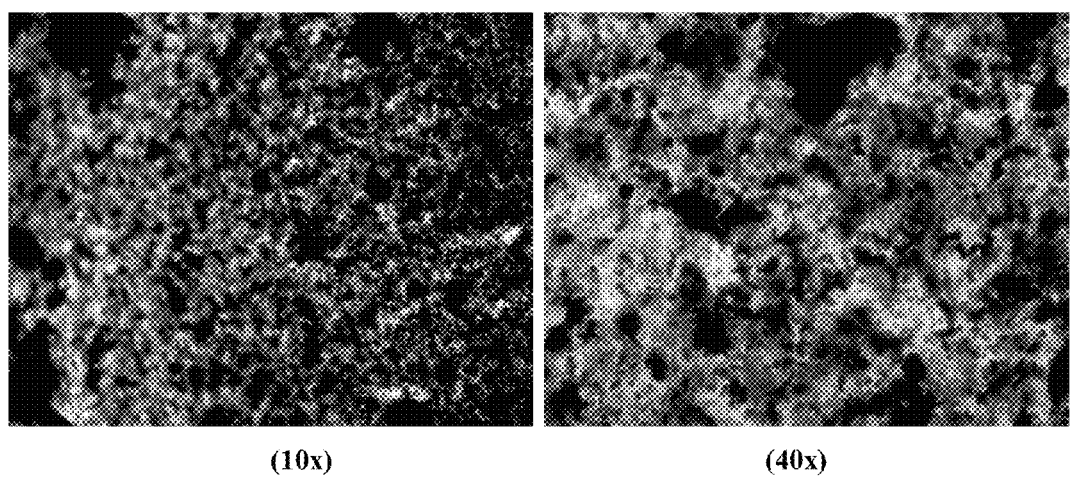

In order to observe the changes of algal cells during the harvesting process, the microscopic images were taken under a light microscopy. FIGS. 21A-21D illustrate the microscopic images of the algae during the harvesting process. The flocculated algae were observed in FIGS. 21A-21D due to high pH 10.6. The magnetite particles were attached with the flocculated algae in the influent before the magnetic separator in FIGS. 21A-21D. Similar images were seen in the effluent before settling in FIG. 21C. FIG. 21D illustrates higher density of algae-magnetite flocs in the effluent after settling. The algae were recovered by lowering the pH to 6.7. All the images confirmed the concept of the magnetic harvesting method proposed above. Magnetic dosage factor and concentration factor variable can be considered for flocculation/coagulation. In certain methods, a 1% magnetite dosage factor can be of use to coagulate suspension cultures of compositions disclosed herein. In other methods, settling time of a culture exposed to magnetite or other agent of use to settle suspension cultures can be considered.

Example 8

Figure 22:
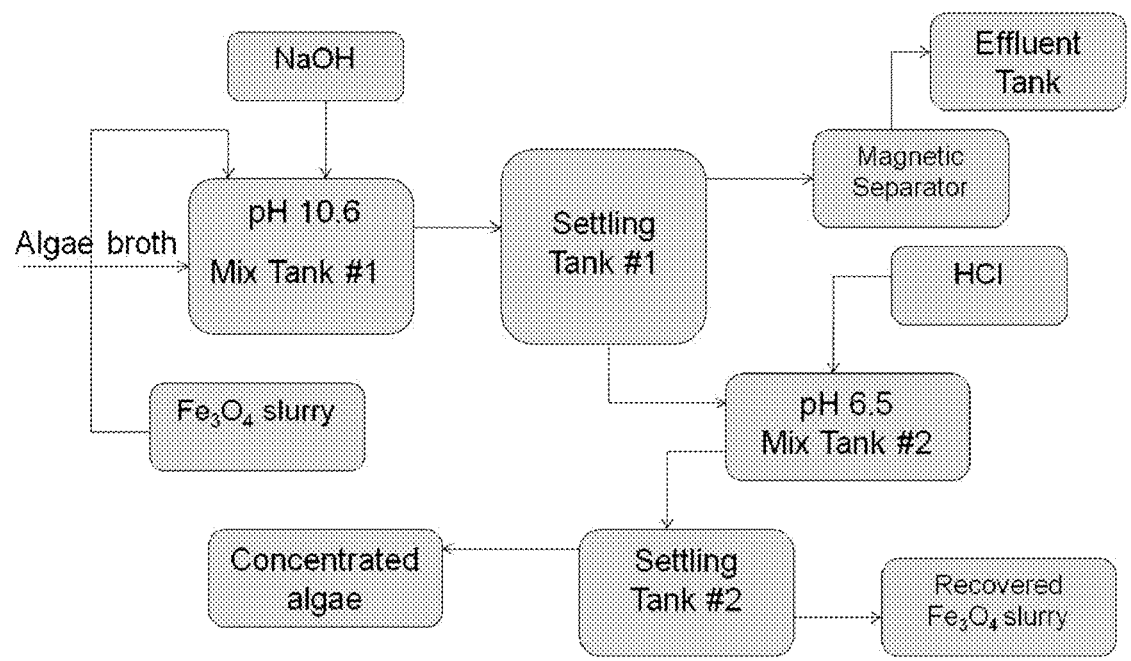
FIG. 22 represents a schematic protocol of suspension culture separation.

A bench-scale unit was designed and set up to test continuous harvesting of algae. A schematic flow chart of algae harvesting is represented in FIG. 22. One test was conducted using this unit.

Algae (*N. salina*) broth (104.8 liters) were pumped into the Mix Tank #1 (5 liter volume) at a flow rate of 1.0 liter/min with a retention time of 5 minutes. Sodium hydroxide (NaOH) solution (5.0 mol/L) and magnetite ($Fe_3O_4$) slurry (35.5% w/w) were flowed into the Mix Tank #1, respectively. The solution pH was kept 10.50-10.61 and magnetite content was 1.05% (w/v) of algae feed. Mechanical mixing was conducted in the Mix Tank #1 at approximately 900 rpm. The algae-magnetite mixture was sent to the Settling Tank #1 at an overflow retention of about 60 minutes. The clear supernatant was overflowed to a Magnetic Separator to remove remaining magnetite and then to an Effluent Tank. The settled algae-magnetite mixture was under flowed into the Mix Tank #2 (volume of 5 liters). The solution pH was adjusted to between 6.47-7.19 using an addition of hydrochloric acid (HCl) at 3.0 mol/L solution into Mix Tank #2. Mechanical mixing was conducted in the Mix Tank #2 at approximate 900 rpm. The resultant mixed algae-magnetite mixture was pumped into the Settling Tank #2 for separation of concentrated algae and magnetite. The thickened algae were overflowed and magnetite slurry was under flowed from the Settling Tank #2. Thus, the concentrated algae and magnetite were recovered.

Figure 23:
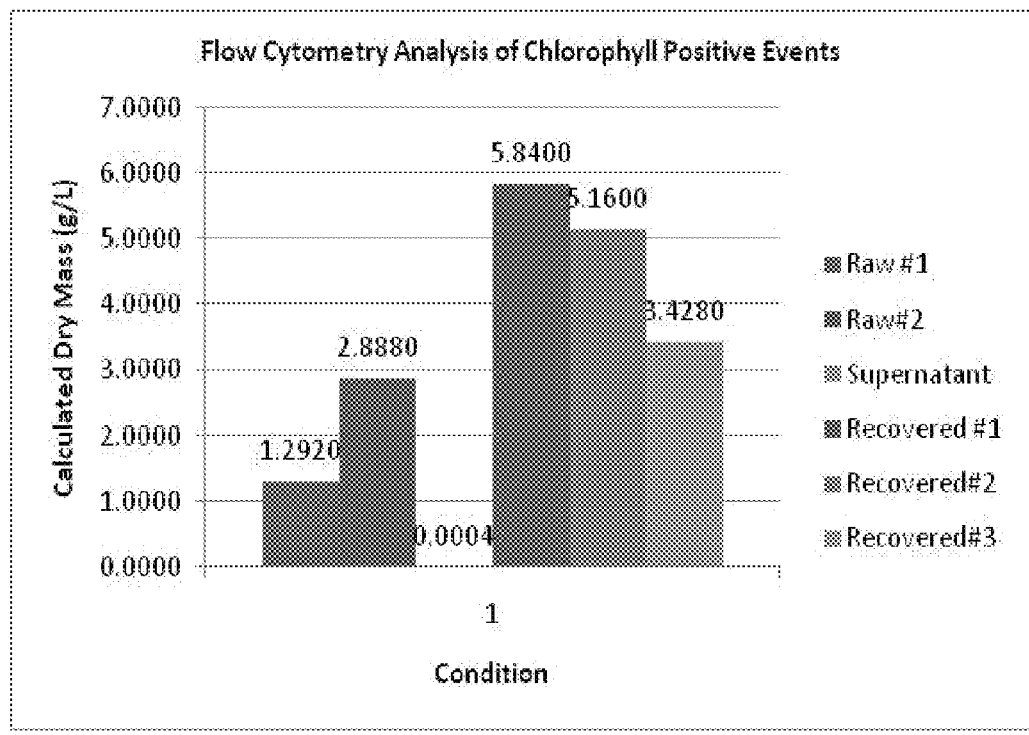
FIG. 23 represents a histogram of algae biomass using flow cytometry analysis.

In this exemplary method, flow cytometry was used to assess algal cultures having been harvest by iron flocculation compared to cultures prior to iron flocculation (see FIG. 23). Table 6 and Table 7 illustrate the results of mass balances of algae and water. The results demonstrated that the majority of water (about 75%) was removed and so algae were concentrated by a factor of 4.0. The algae density in supernatant effluent was very low at 0.0004 g/L, indicated that algal loss in the supernatant at 0.017%. Thus algae recovery was over 99% obtained in this test. A schematic flow chart of algae harvesting is represented in FIG. 22.

TABLE 6

Algae mass balance

|  | Volume (liter) | Dry mass (g/L) | Dry biomass (g) |
|---|---|---|---|
| Raw Algae #1 | 90.8 | 1.292 | 117.3 |
| Raw Algae #2 | 50.0 | 2.888 | 144.4 |
| Recovery Algae #1 | 18.93 | 5.840 | 110.6 |
| Recovery Algae #2 | 16.28 | 5.160 | 84.0 |
| Algae #3 in recovered magnetite slurry | 3.4 | 17.14 | 58.3 |
| Supernatant | 113.17 | 0.0004 | 0.045 |
| Total amount in effluent (g) |  |  | 252.9 |
| Total amount in influent (g) |  |  | 261.7 |
| Algae loss in supernatant (%) |  |  | 0.017 |
| Error (%) |  |  | −3.4 |

TABLE 7

Water volume balance

|  | Volume (liter) |
|---|---|
| Influent | |
| Water from raw algae broth | 140.8 |
| Water from magnetite slurry | 2.68 |
| Water from base solution | 0.79 |
| Water from acid solution | 1.38 |
| Influent Total | 145.7 |
| Effluent | |
| Water from supernatant | 113.17 |
| Water in recovered algae | 35.2 |
| Water in recovered magnetite slurry | 2.96 |
| Effluent Total | 151.3 |
| Error (%) | +3.8 |

Example 9

Removal of Magnetite Residues from Settled Supernatant

In another exemplary experiment, methods for recycling and reusing media are contemplated. Magnetite residues in supernatant were observed after gravity settling under a microscope. Medium pH and associated magnesium hydroxides on the magnetite settling were investigated. The results suggest that magnesium hydroxide precipitates might be a negative factor on the magnetite settling in terms of water removal. It was attempted to remove magnetite residues from the supernatant using pH adjustment, reuse of magnetite and magnetic capture. Magnetite residues were not completely removed at low pH by reusing magnetite particles. Further removal of the magnetite residues was attempted by magnetic capture through a strong magnetic field formed by two permanent magnets. Supernatant containing very few magnetite particles or essentially magnetite-free could be obtained after the magnetic capture. It is suggested to use a high gradient magnetic filter in scale-up operation. Medium could be recycled for algae cultivation after the magnetite residues are removed.

Use of Stronger Magnetic Field

In one example, a strong magnetic field was used to capture magnetite from a supernatant. In this example, a strong magnetic field could be formed using two magnets (e.g. permanent magnet from Bangs Laboratories Inc.) with a flat or compressed vessel secured between the magnets as demonstrated in FIG. 24. Using this type of set-up, supernatant sample was added to the vessel and left for about 15 min (e.g. aged). The essentially clear supernatant was decanted while maintaining the set-up while the magnetite residues were captured within the walls of the vessel for recovery of magnetite. These methods could be used for rapid consolidation and harvesting of a culture for testing or scale-up for harvesting and reuse of media etc. In addition, the treated supernatants were centrifuged (for example at 6,000 rpm for 10 min) to get concentrated samples for microscopic observation and potential testing.

Figure 24:
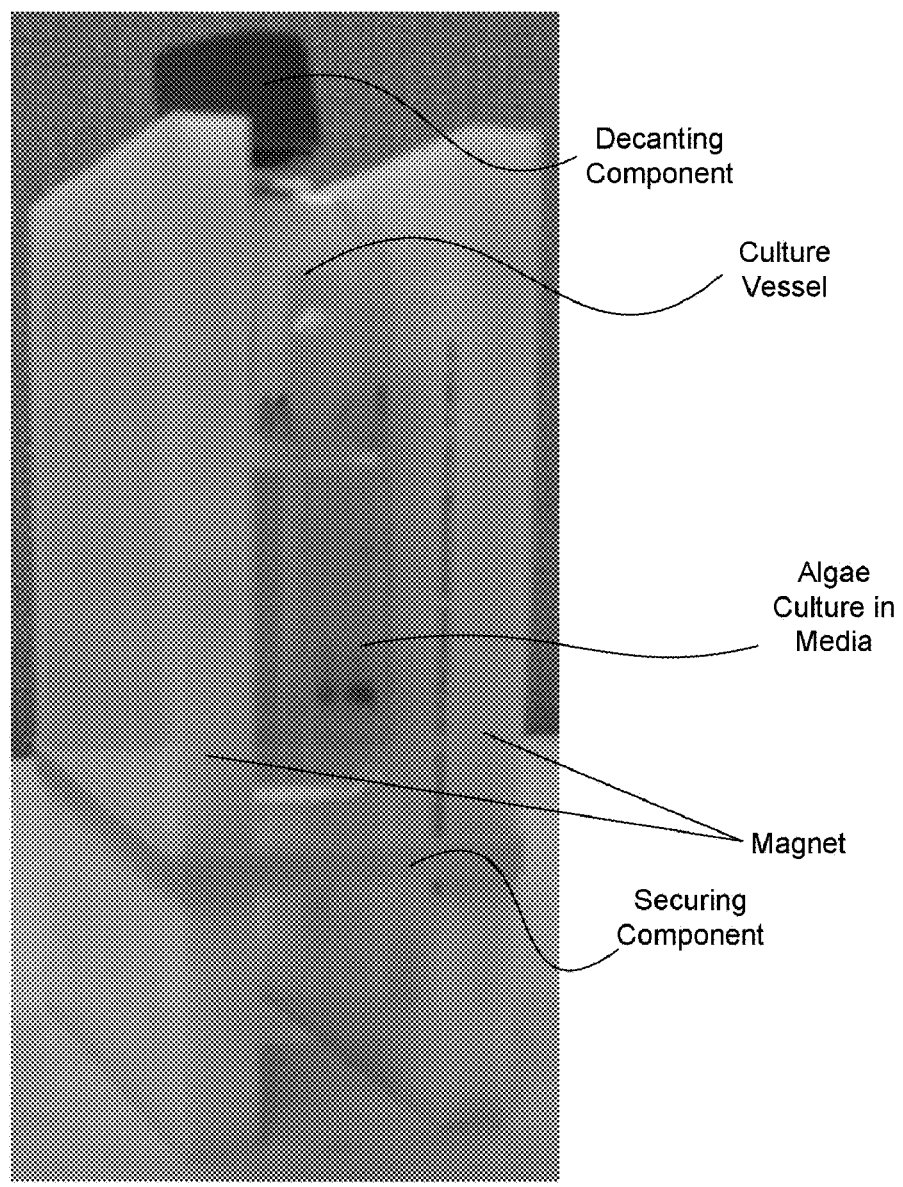
FIG. 24 represents harvesting of a culture using an exemplary apparatus disclosed herein.
Figure 25A:
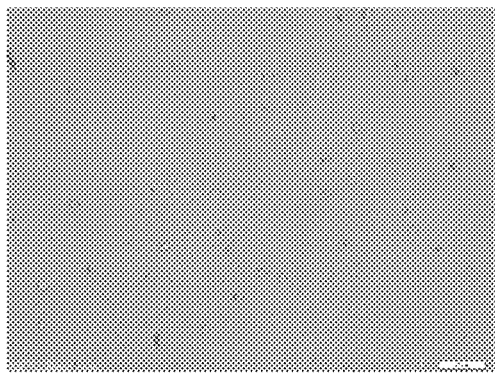
FIGS. 25A and 25B are photographs illustrating the lack of certain particles present after magnetic separation.
Figure 25B:
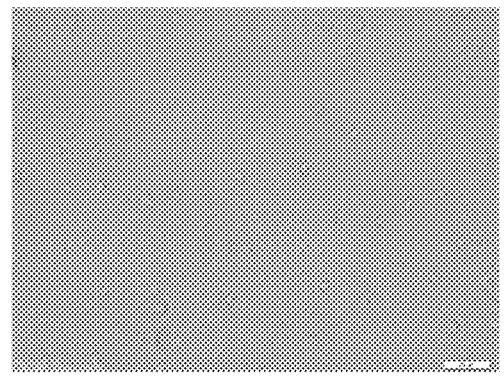

Some magnetite particles were captured by the strong magnetic field as demonstrated in FIG. 24, indicating that the magnets under the strong magnetic field can capture magnetite residues from the supernatant. FIGS. 25A and 25B illustrate an attempt to observe potential particle residues under a microscope using two representative samples (25A and 25B). No magnetite particles were observed in the images, suggesting that very few magnetite particles or free magnetite were present in the treated supernatant samples because they were essentially removed by harvesting.

Materials and Methods

In certain methods, various chemicals, procedures and materials may be used, including, but not limited to, the following:

Examples of Algae: *Nannochloropsis oculata, Nannochloropsis salina*
Magnetite [Iron (II, III) oxide] powder (<5 μm) from Aldrich (e.g. Cat #: 310069)
Magnetite [Iron (II, III) oxide] powder from Pirox 200
Tungsten (W) (Sigma-Aldrich; e.g. Cat #: 510106)
Reactive Blue 4 (Sigma-Aldrich; e.g. Cat #: 244813)
Calcium hydroxide ($Ca(OH)_2$) (Fluka; e.g. Cat #: 21181)
Ammonium hydroxide ($NH_4OH$) (Sigma-Aldrich; e.g. Cat #: 221228)
Permanent magnet from Bangs Laboratories Inc. (e.g. BioMag® Flask Separator, Cat #: MS004)
Magnetic Separator of Permanent Magnet from S. G. Frantz Co. Inc. (Model PQ-2)

Algal Growth:
For Example 8:
Raw algae (e.g. *N. salina*) reserved in tanks with air bubbling under lamps in Example 8
Magnetite stock slurry: 35.5% (w/w)—magnetite addition of 1.05% (w/v) of algae feed
Supernatant passed through a Magnetic Separator pH: harvesting pH=10.50-10.61; recovered pH=6.47-7.19
Influent flow rate: 1.0 L/min All of the COMPOSITIONS and/or METHODS and/or APPARATUS disclosed and claimed herein can be made and executed without undue experimentation in light of the present disclosure. While the compositions and methods of this invention have been described in terms of preferred embodiments, it will be apparent to those of skill in the art that variation may be applied to the COMPOSITIONS and/or METHODS and/or APPARATUS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for harvesting suspension organism cultures from a liquid composition comprising, providing an agent to a suspension culture at a pH of at least 9.0 to about 11.5 to form a complex of agent-organism; capturing the agent-organism complex using one or more of a separator or gravity, wherein the liquid of the liquid composition becomes substantially clear after capture; and removing the organism from the agent by providing an environment having a pH of about 6.0 to about 7.5.

2. The method of claim 1, further comprising, harvesting the organism for reculturing.

3. The method of claim 1, further comprising collecting the agent for reuse.

4. The method of claim 1, wherein the agent comprises iron oxides, iron, steel, silica, tungsten, and magnesium agents.

5. The method of claim 1, wherein the agent comprises a particle size of 0.5 μm to 10 μm.

6. The method of claim 1, wherein the suspension organisms comprise algae, bacteria, fungi and yeast.

7. The method of claim 1, wherein modulating the pH of the liquid composition comprises introducing an agent to the liquid composition comprising one or more of inorganic bases, inert gas, acids and acid gas stripping.

8. The method of claim 1, wherein capturing the agent-organism complex comprises using a magnetic separator, wherein the liquid of the liquid composition becomes substantially clear after capture magnetic separation of the agent-organism complex.

9. The method of claim 4, wherein the agent comprises a magnesium agent and the complex of agent-organism is captured by a magnetic separator.

* * * * *